United States Patent [19]

Beach et al.

[11] Patent Number: 6,037,136
[45] Date of Patent: *Mar. 14, 2000

[54] INTERACTIONS BETWEEN RAF PROTO-ONCOGENES AND CDC25 PHOSPHATASES, AND USES RELATED THERETO

[75] Inventors: David H. Beach, Huntington Bay; Konstantin Galaktionov, Cold Spring Harbor, both of N.Y.; Catherine Jessus, Paris, France

[73] Assignee: Cold Spring Harbor Laboratory, Cold Spring Harbor, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/328,239

[22] Filed: Oct. 24, 1994

[51] Int. Cl.⁷ .................................................. G01N 33/573
[52] U.S. Cl. .............................. 435/7.4; 435/7.8; 435/15; 435/21
[58] Field of Search .................................. 435/7.1, 21, 29, 435/254.2, 254.11, 32, 69.1, 7.4, 7.8, 15; 530/350; 536/23.1

[56] References Cited

U.S. PATENT DOCUMENTS

| 5,405,941 | 4/1995 | Johnson | 530/350 |
| 5,443,962 | 8/1995 | Draetta et al. | 435/29 |
| 5,532,167 | 7/1996 | Cantley et al. | 436/89 |

FOREIGN PATENT DOCUMENTS

WO 93/10242 A1 5/1993 WIPO.

OTHER PUBLICATIONS

Galaktionov et al, Genes and Devel vol. 9:1046–1058, 1995.

*Primary Examiner*—Donna Wortman
*Attorney, Agent, or Firm*—Matthew P. Vincent; Beth E. Arnold; Foley, Hoag & Eliot

[57] ABSTRACT

The present invention derives from the discovery that CDC25 phosphatases and Raf proteins are able to physically interact to form protein-protein complexes, with the Raf protein mediating the activation of CDC25 phosphatases. The present invention provides both cell-free and cellular assays for detecting agents which modulate the ras-dependent activation of CDC25, as for example, by affecting the binding of a CDC25 protein with Raf, or Raf-associated complexes. Also disclosed is a method for transforming/immortalizing cells, particularly primary cell cultures.

16 Claims, No Drawings

INTERACTIONS BETWEEN RAF PROTO-ONCOGENES AND CDC25 PHOSPHATASES, AND USES RELATED THERETO

BACKGROUND OF THE INVENTION

The progression of a proliferating eukaryotic cell through the cell-cycle checkpoints is controlled by an array of regulatory proteins that guarantee that mitosis occurs at the appropriate time. Protein phosphorylation is the most common post-translational modification that regulates processes inside the cells, and a large number of cell cycle transitions are regulated by, in addition to protein-protein interactions, the phosphorylation states of various proteins. In particular, the execution of various stages of the cell-cycle is generally believed to be under the control of a large number of mutually antagonistic kinases and phosphatases. A paradigm for these controls is the CDC2 protein kinase, whose activity is required for the triggering of mitosis in eukaryoitc cells (for reviews, see Hunt (1989) *Curr. Opin. Cell Biol.* 1:268–274; Lewin (1990) Cell 61:743–752; and Nurse (1990) *Nature* 344:503–508). During mitosis, the CDC2 kinase appears to trigger a cascade of downstream mitotic phenomena such as metaphase alignment of chromosomes, segregation of sister chromatids in anaphase., and cleavage furrow formation. Many target proteins involved in mitotic entry of the proliferating cell are directly phosphorylated by the CDC kinase. For instance, the CDC2 protein kinase acts by phosphorylating a wide variety of mitotic substrates involved in regulating the cytoskeleton of cells, such that entry into mitosis is coordinated with dramatic rearrangment of cytoskeletal elements.

The CDC2 kinase is subject to multiple levels of control. One well-characterized mechanism regulating the activity of CDC2 involves the phosphorylation of tyrosine, threonine, and serine residues; the phosphorylation level of which varies during the cell-cycle (Draetta el al. (1988) *Nature* 336:738–744; Dunphy et al. (1989) *Cell* 58:181–191; Morla et al. (1989) *Cell* 58:193–203; Could et al. (1989) *Nature* 342:39–45; and Solomon et al. (1990) *Cell* 63:1013–1024). The phosphorylation of CDC2 on Tyr-15 and Thr-14, two residues located in the putative ATP binding site of the kinase, negatively regulates kinase activity. This inhibitory phosphorylation of CDC2 is mediated at least in part by the wee1 and mik1 tyrosine kinases (Russel et al. (1987) *Cell* 49:559–567; Lundgren et al. (1991) *Cell* 64:1111–1122; Featherstone et al. (1991) *Nature* 349:808–811; and Parker et al. (1992) *PNAS* 89:2917–2921). These kinases act as mitotic inhibitors, over-expression of which causes cells to arrest in the G2 phase of the cell-cycle. By contrast, loss of function of wee1 causes a modest advancement of mitosis, whereas loss of both wee1 and mik1 function causes grossly premature mitosis, uncoupled from all checkpoints that normally restrain cell division (Lundgren et al. (1991) *Cell* 64:1111–1122).

As the cell is about to reach the end of G2, dephosphorylation of the CDC2-inactivating Thr-14 and Tyr-15 residues occurs leading to activation of the CDC2 complex as a kinase. A stimulatory phosphatase, known as CDC25, is responsible for Tyr-1 5 and Thr-14 dephosphorylation and serves as a rate-limiting mitotic activator. (Dunphy et al. (1991) *Cell* 67:189–196; Lee et al. (1992) *Mol. Biol. Cell.* 3:73–84; Millar et al. (1991) *EMBO J* 10:4301–4309; and Russell et al. (1986) *Cell* 45:145–153). Recent evidence indicates that both the CDC25 phosphatase and the CDC2-specific tyrosine kinases are detectably active during interphase, suggesting that there is an ongoing competition between these two activities prior to mitosis (Kumagai et al. (1992) *Cell* 70:139–151; Smythe et al. (1992) *Cell* 68:787–797; and Solomon et al. (1990) *Cell* 63:1013–1024). This situation implies that the initial decision to enter mitosis involves a modulation of the equilibrium of the phosphorylation state of CDC2 which is likely controlled by variation of the rate of tyrosine dephosphorylation of CDC2 and/or a decrease in the rate of its tyrosine phosphorylation. A variety of genetic and biochemical data appear to favor a decrease in CDC2-specific tyrosine kinase activity near the initiation of mitosis which can serve as a triggering step to tip the balance in favor of CDC2 dephosphorylation (Smythe et al. (1992) *Cell* 68:787–797, Matsumoto et al. (1991) *Cell* 66:347–360; Kumagai et al. (1992) *Cell* 70:139–151; Rowley et al. (1992) *Nature* 356:353–355; and Enoch et al. (1992) *Genes Dev.* 6:2035–2046). Moreover, recent data suggests that the activated CDC2 kinase is responsible for phosphorylating and activating CDC25. This event would provide a self-amplifying loop and trigger a rapid increase in the activity of the CDC25 protein, ensuring that the tyrosine dephosphorylation of CDC2 proceeds rapidly to completion (Hoffmann et al. (1993) *EMBO J* 12:53).

Studies of the meiotic cell cycle have likewise demonstrated the role of inhibitory phosphorylation of Tyr-15 and/or Thr-14 on induction of meiosis, and indicate that activation of meiotic cyclin dependent kinases (CDK)/cyclin complexes (known as maturation promoting factor, MPF) is mediated by the antagonistic actions of the Wee1 protein kinase and the CDC25 tyrosine phosphatase. MPF, like the mitotic CDK/cyclin complexes, is activated by removing the inhibitory tyrosine phosphate from a pool of preMPF. In accord with this scheme, preMPF complexes can be isolated from unstimulated oocytes and converted into active MPF in vitro by treating them with purified CDC25. For instance, in Xenopus oocytes that are blocked in prophase of the first meiotic division, CDC2 kinase is complexed with mitotic cyclins but is present in an inactive, Thr14 and Tyr15 phosphorylated state. Upon stimulation with progesterone, or insulin, oocytes undergo the transition into meiosis (maturation), that is, effect dephosphorylation of CDC2 on the Thr14 and Tyr15 residues and thus the activation of the CDC2 histone H1 kinase (Dunphy et al. (1989) *Cell* 58:181–191; and Gautier et al. (1989) *Nature* 339:626–629). As above, the initiation of maturation probably reflects a change in the balance between the opposing activities of CDC25 and Wee 1.

In addition to internal regulatory signals, such as those networks which guarantee that the successive events of each cell-cycle occur in a faithful and punctual manner, cell proliferation may also be regulated by chains of events that begin with the interaction of growth factors with specific growth factor receptors located in the plasma membrane of the cell. The binding of a growth factor by its cognate receptor induces the receptor to generate signals inside the cell, and, by propagation along signal transduction pathways, can result in the activation of a variety of intracellular enzymes, mainly protein kinases and phosphatases. Changes in protein phosphorylation, mediated by the signal transduction process, can lead to the transcription of early response genes that encode transcription factors, which in turn induce the transcription of delayed response genes. The products of the delayed response genes include cell cycle regulatory proteins, such as $G_1$ cyclins and cyclin dependent kinases. However, certain aspects of growth factor induction have not previously been elucidated. For instance, it is not apparent from the literature how it is that growth factors and the signals they induce antagonize the ability of tumor suppressor gene products, like the retinoblastoma protein (Rb), to inhibit the transcription of early response genes.

SUMMARY OF THE INVENTION

One aspect of the present invention relates to assays which can be used to identify agents which are either agonists or antagonists of the normal cellular function of a CDC25 phosphatase, or of their role in the pathogenesis of cellular proliferation and/or differentiation and disorders related thereto, as mediated by Raf kinase-dependent activation of the phosphatase. In general, the assay evaluates the ability of a compound to modulate binding and/or enzymatic activation of a CDC25 phosphatase by a Raf kinase, or kinase which is activated by the Raf kinase, In one embodiment, the method is arranged for identifying a compound which is an inhibitor of ras-mediated activation of a CDC25 phosphatase. For instance, the assay can be carried out including the steps of:
 a) generating a combination including:
  1) a test agent to be assessed;
  2) a cell-free preparation of a CDC25 phosphatase,
  3) a cell-free preparation of a kinase from a ras-mediated signal transduction cascade, which kinase phosphorylates the CDC25 phosphatase; and
  4) a substrate of the CDC25 phosphatase;
 b) maintaining the combination under conditions appropriate for the kinase to phosphorylate the CDC25 phosphatase and for an activated CDC25 phosphatase to convert the substrate to product; and
 c) measuring the conversion of the substrate to product.
In such embodiments of the subject assay, a statistically significant decrease in the conversion of the substrate to product in the combination, relative to a control comprising the CDC25 phosphatase, the kinase, and the substrate but lacking the test agent, indicates that the test compound is an inhibitor of ras-mediated activation of the CDC25 phosphatase. In a preferred embodiment, the kinase is a Raf kinase, e.g. a Raf-1 kinase, a Raf-A kinase or a Raf-B kinase, and, even more preferably, is a human Raf kinase. For instance, the kinase can include a polypeptide having an amino acid sequence represented in SEQ ID No. 4 (human Raf1), or a CDC25-binding portion thereof, such as the CR3 domain.

In other embodiments, the kinase can be selected from the group consisting of MAPK/ERK kinases (MEKs), mitogen-activated protein kinases (MAPKs), and MAP kinases (ERKs).

The source of the CDC25 phosphatase can also vary from one embodiment of the assay to the next, but will, in general, preferably be a mammalian CDC25, and in particular, will be selected from the group consisting of CDC25A, CDC25B, and CDC25C, such as the human CDC25 phosphatase represented in SEQ ID No. 1 (CDC25A), SEQ ID No. 2 (CDC25B) or SEQ ID No. 3 (CDC25C).

In certain embodiments of the assay, as described below, either or both of the CDC25 phosphatase and the kinase can be provided in the combination as fusion proteins. Such fusion proteins can provide, for example, a means for detecting the protein to which it is attached, as well as a means for immobilizing the protein on an insoluble matrix. In an exemplary embodiment, the fusion protein is a glutathione-S-transferase fusion protein.

The cell-free preparations of the CDC25 phosphatase and the kinase can be provided to the combination, for example, in the form of cell-lysates, but may also be in the form of a purified or semi-purified protein preparation.

In preferred embodiments of the assay, the conversion of substrate to product provides a colorimetric indicator of phosphatase activity. For example, the assay can be carried out using a substrate for the CDC25 phosphatase comprising a p-nitrophenyl-phosphate. Alternatively, it may be more desirable to provide screens wherein the substrate of the CDC25 phosphatase is a physiological substrate of the enzyme, such as an inactive (e.g. phosphorylated) CDK/cyclin complex.

In yet another embodiment of the assay, an inhibitor of the interaction between a CDC25 phosphatase and a kinase from a ras-mediated signal transduction cascade (such as Raf1), can be detected as above, except that instead of detecting the activation of the enzymatic activity of the CDC25 phosphatase, the formation of a complex including the Kinase and the CDC25 polypeptide is detected. As above, a statistically significant decrease in the formation of the complex in the presence of the test agent, relative to the formation of the complex in the absence of the test agent, is indicative of the test agent being an inhibitor of the interaction between the kinase and the CDC25 phosphatase.

In a preferred embodiment, the assay comprises a Raf-kinase, such as Raf1. Moreover, in certain embodiments, it may be desired to provide, in addition to the Raf kinase, other cellular proteins which associate with the Raf kinase, CDC25 or both. Exemplary proteins for supplementing the combination are selected from a group consisting of MAPK/ERK kinases (MEKs), mitogen-activated protein kinases (MAPKs), MAP kinases (ERKs), bcl-2, cyclins, a cyclin-dependent kinases (CDK), or a combination thereof.

In still further embodiments, the affects of a test agent on CDC25 activity can be ascertained from whole cells treated with the test agents. According to this embodiment, a cell which expresses both a CDC25 and a Raf kinase is contacted with the agent, the cell is subsequently lysed after a period of incubation, and the amount of CDC25/Raf complexes in the lysate is detected. Alternatively, the enzymatic activity of the CDC25 phosphatase is scored in the lysate for using a substrate for that enzyme. Agents which disrupt the interaction of the Raf kinase and the CDC25 phosphatase can be detected by comparing the level of protein complexes formed or the rate of substrate conversion in the lysate.

Yet another embodiment of the subject method provides an interaction trap assay (or two hybrid assay) for identifying a compound which is an inhibitor of the interaction between a CDC25 phosphatase and a Raf kinase. In a preferred embodiment, the assay comprises the steps of:
 i) providing an interaction trap system in a cell including
  a) a first fusion protein comprising a Raf protein portion which binds a CDC25 protein and a first portion of a transcriptional activator protein,
  b) a second fusion protein comprising a CDC25 protein portion and a second portion of a transcriptional activator protein, and
  c) a reporter gene which expresses a detectable protein when the reporter gene is activated by a protein-protein complex of the first and second fusion proteins under conditions expression of the reporter gene is sensitive to interactions between the Raf protein portion of the first fusion protein and the CDC25 protein portion of the second polypeptide;
 ii) contacting the cell with a test agent; and
 iii) detecting the expression of the reporter gene in the presence of the candidate agent.
Comparing the expression of the reporter gene in the presence of the candidate agent to its expression in the absence of the candidate agent, provides a basis for determining the ability of a test agent to inhibit the Raf/CDC25 interaction. In general, a statistically significant decrease in the level of reporter gene expression in the presence of the candidate agent is indicative of the test agent being an inhibitor of interactions between the CDC25 phosphatase and the Raf kinase.

Yet another embodiment of the subject assay comprises a cell-based system which ascertains the effects of a test compound on proliferative or growth effects attributable to ras-dependent activation of CDC25. For instance, the assay can comprise the steps of.

i) generating a host cell expressing
   a) a recombinant CDC25 phosphatase, and
   b) an oncogenic form of a ras protein or a kinase from a ras-mediated signal transduction cascade, which oncogenic protein phosphorylates the CDC25 phosphatase;
     which host cell manifests abnormal proliferation or growth characteristics due to activation of the CDC25 phosphatase by the oncogenic protein;
ii) contacting the host cell with a test agent to be assessed; and
iii) ascertaining changes in proliferation or growth characteristics of the host cell which are dependent on the activation of the CDC25 phosphatase A change in the CDC25-dependent proliferation or growth characteristics of the host cell relative to a host cell which is not treated with the test agent, indicates that the test agent is a modulator of ras-mediated activation of the CDC25 phosphatase.

Another aspect of the invention pertains to methods for treating proliferative and/or differentiative disorders which arise from cells which, despite aberrant growth control, still require CDC25 for cell growth. There are a wide variety of pathological cell proliferative and differentiative conditions which may be treatable with regimens that include agents able to modulate Raf-mediated CDC25 activation. For instance, agents identified in the assays of the present invention can provide therapeutic benefits, with the general strategy being the inhibition of anomalous cell proliferation.

Yet another aspect of the invention pertains to a method of transforming cells either in vivo or in vitro. As demonstrated below, CDC25 can cooperate with oncogenically activated Ras to promote transformation of cells. Accordingly, contacting a cell with agents that agonize Raf-mediated CDC25 activation, such as through co-transfection of the cell with expression vectors encoding a CDC25 and an oncogenic Ras or Raf protein, can be used to transform, and even immortalize, cells from in vitro cultures Such cultures provide, for example, a source of implantable cells, as well as make available systems for screening drugs and determining cytotoxicity.

Other features and advantages of the invention will be apparent from the following detailed description, and from the claims. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press:1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986).

DETAILED DESCRIPTION OF THE INVENTION

Protein phosphorylation is the most common post-translational modification that regulates processes inside cells and plays a key role in regulating the cell cycle engine. Protein kinases add phosphates to proteins by transferring phosphate groups from, for example, ATP, to hydroxyl groups on amino acid side chains; protein phosphatases remove the phosphate group. Phosphorylation of a given amino acid in a protein can have a variety of effects: activating or inactivating a protein's enzymatic activity, or altering a protein's affinity for binding to other proteins. In dividing eukaryotic cells, circuits of regulatory kinases and phosphatases oversee both the initiation and completion of the major transitions of both the meiotic and mitotic cell-cycles.

It is now clear that molecular information arriving at the surface of a cell can be transmitted as a signal from activated receptor tyrosine kinases in the cytoplasmic membrane to distal locations within the cell. The Ras and Raf1 proto-oncogenes, for instance, are essential elements of mitogenic and other signal transduction pathways that become activated through various receptor and non-receptor tyrosine kinases (Stacey et al. (1991) *Oncogene* 6:2297–2304; Wood et al. (1992) *Cell* 68:1041–1050; Thomas et al. (1992) *Cell* 68:1031–1041). It has been shown that the Ras protein binds GTP and functions to promote membrane localization and activation of the Raf1 protein kinase (Stokoe et al. (1994) *Science* 264:1463–1467; Leevers et al. (1994) *Nature* 369:411–414), which in turn phosphorylates and activates MEK (Kyriakis et al. (1992) *Nature* 358:417–421; Howe et al. (1992) *Cell* 71:335–342; and Dent et al. (1992) *Science* 257:1404–1407), again followed by MFK-dependent phosphorylation and activation of MAP kinases (ERKs) (see, for example, Ahn et al. (1991) *J.Biol Chem* 266:4220–4227 (1991); Kosako et al. (1992) *EMBO J* 11:2903–2908 (1992); Gomez et al. (1991) *Nature* 351:69–72). These events constitute a signal transduction kinase "cascade", which is believed to be a central element of the cellular response to the extracellular stimuli including various mitogens (Nishida et al. (1993) *Trends Biochem. Sci.* 18:128–131; Davis, R. J. (1993) *J. Biol. Chem.* 268:14553–14556.

The Raf genes encode a family of cytoplasmic proteins (A-Raf, B-Raf and c-Raf1, as well as concomitant orthologs such as D-Raf) with associated serine/threonine kinase activities. Raf1 (72–74kd), the protein product of the c-Ras1 gene, is found to be ubiquitously expressed, while A-Raf (68kd) and B-Raf (95kd) have each have a more tissue specific distribution, with A-Raf being most abundant in epididymis, urogenital tissue and ovary, and B-Raf in fetal brain and adult cerebrum and testis. The Raf proteins are cytoplasmically localized and play a critical role in the transmission of signals from cell surface receptors. For instance, Raf1 has been shown to be an important mediator of signals involving cell growth transformation and differentiation. It is activated in response to a wide variety of extracellular stimuli such as insulin, nerve growth factor (NGF), platelet derived-growth factor (PDGF), and in response to expression of oncogenes, v-src and v-ras.

In frog oocytes, Raf1 has been implicated in meiotic maturation that is mediated by progesterone and receptor tyrosine kinases (RTK) (Fabian et al. (1993) *J Cell Biol.* 122:645–652; Muslin et al. (1993) *Mol. Cell Biol.* 13:4197–4202; Heidecker et al. (1991) *Adv. Cancer Res*, 58:53–73). Introduction of oncogenic forms of either Ras or Ras1 causes precocious maturation of Xenopus oocytes, associated with activation of the cyclinB/CDC2 kinase.

Raf1 is a 648 amino acid protein (see SEQ ID NO: 4, human Raf1) with intrinsic serine-threonine kinase activity. Analysis of transformed cells transfected with DNA from similar human tumors has revealed that the presence of truncated Raf sequences (Stanton et al. (1987) *Mol. Cell Biol.* 7:1171–1179; and Tahira et al. (1987) *Nuc. Acids Res.* 15:4809–4820). A detailed deletional analysis revealed that the transforming potential of the C-terminal kinase domain of Raf1 is suppressed by a regulatory N-terminal domain. Independent studies have demonstrated that deletion of the entire N-terminal domain (residues 2–305 of the protein sequence, Stanton et al. (1989) *Mol. Cell Biol.* 9:639–647) or deletion of just 55 amino acids of a serine-threonine rich domain (residues 225–280, Ishikawa et al. (1988) *Oncogene* 3:653–658) resulted in truncated Raf proteins that are capable of transforming cells. Based on structure-function analysis and by comparing conserved sequences, the Raf1 protein kinase has been divided into three domains, conserved regions 1, 2 and 3 (CR1, CR2 and CR3, Heidecker et al. (1990) *Mol Cell Biol.* 10:2503–2512). The first of these domains, CR1, contains a conserved cysteine motif (identified by Ishikawa et al., supra), similar in sequence to the lipid-binding cysteine motif identified in protein kinase C (PKC).

The second domain contains a conserved serine-threonine rich tract, CR2, with unknown function. The third domain, CR3, is the conserved kinase domain of Raf1. CR3 displays extensive homology with other known kinases (Hanks et al. (1980) *Science* 241:42–52). Removal of the N-terminal "regulatory" portion, consisting of CR1 and CR2, of the Raf1 protein results in a C-terminal kinase domain (CR3) which is constitutively active and has transforming potential (Stanton et al., supra; and Heidecker et al., supra).

The present invention derives from the discovery that CDC25 phosphatases and Raf proteins are able to physically interact to form protein-protein complexes, with the Raf protein mediating the activation of CDC25 phosphatases. Given the apparently significant role that Raf kinases may play in the regulation of cellular growth and transformation by functioning as intermediates in signal transduction processes, the discovery that a Raf kinase modulates the activity of an enzyme critical for both mitosis and meiosis provides an important target for developing agents which either disrupt, or alternatively, potentiate the mitogenic effects of various extracellular stimuli. For example, as described below, disruption of Raf1-dependent activation of CDC25 represents a potential therapeutic approach for treating a number of proliferative, and in some instances, differentiate disorders, as well as promoting survival of certain cells. In similar fashion, such agents can be used to control the effect of various extracellular stimuli, such as growth factor induction of cultured cells and tissues. Accordingly, the present invention provides both cell-free and cellular assays for detecting agents which modulate the ras-dependent activation of CDC25, as for example, by affecting the binding of a CDC25 protein with Raf, or Raf-associated complexes.

Moreover, as described below, CDC25 can cooperate with oncogenically activated Ras to promote transformation of cells. Accordingly, contacting a cell with agents that agonize Raf-mediated CDC25 activation, such as through co-transfection of the cell with expression vectors encoding a CDC25 and an oncogenic Ras or Raf protein, can be used to transform, and even immortalize, cells from in vitro cultures.

In this manner, it will be possible to transform primary cell cultures, which ordinarily may be limited in proliferation to only a few generations, to cultures which can be passaged many times, and, if immortalized, can be maintained in culture indefinitely. The subject method can be of considerable value, for example, in transforming cells obtained from tissue samples and biopsies, and may prove particularly useful for immortalizing cells which are typically difficult to maintain in a given phenotypic state in culture, such as certain kidney or pancreatic cells as well as embryonic cells.

For convenience, certain terms employed in the specification, examples, and appended claims are collected here.

As used herein, the term "transfection" refers to the introduction of a nucleic acid, e.g., an expression vector, into a recipient cell by nucleic acid-mediated gene transfer.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the present disclosure is intended to include other forms of expression vectors which serve equivalent functions and which become known in the art subsequently hereto.

A "chimeric protein" or "fusion protein" is a fusion of a first amino acid sequence encoding, for example a CDC25 phosphatase or a Raf kinase, with a second amino acid sequence defining a domain foreign to and not substantially homologous with any domain of a CDC25 or Raf protein. A chimeric protein may present a foreign domain which is found (albeit in a different protein) in an organism which also expresses the first protein, or it may be an "interspecies", "intergeneric", etc. fusion of protein structures expressed by different kinds of organisms. In an illustrative embodiments, the present invention provides, in various assay formats, CDC25-GST and/or Raf/GST fusion proteins.

The term "transformed cell" is art recognized and refers to cells which exhibit at least the following properties.

(i) increased capacity to persist in serial subcultures;

(ii) increased growth rate in vitro, and (iii) loss of contact inhibition.

The term "immortal cell" or "immortalized cell" is art recognized, and is used to refer to transformed cells which are able to persist in serial subcultures indefinitely.

The term "Ras protein" or "Raf kinase" refers to an art-recognized family of proto-oncogenes that exhibit serine/threonine kinase activity, which family includes the human c-Ras -1 (or Raf1), A-Raf and B-Raf kinases (see, for example, Beck et al. (1987) *Nuc Acid Res* 15:595–609; Ikawa et al. (1988) *Mol Cell Biol* 8:2651–2654; Wolfes et al. (1989) *Science* 245:740–743; and Storm et al. (1990) *Oncogene* 5:345–351), as well as the corresponding orthologs from other eukaryotic species. The sequence for recombinant Raf kinase genes, and methods for expressing and purified Ras kinases are generally known in the art.

The term "CDC25 protein" or "CDC25 phosphatase" refers to an art-recognized family of phosphatases which possess, for example, an enzymatic activity for dephosphorylating CDKs. Identified initially in *S. pombe*, a significant number of homologs of the fission yeast CDC(25 have been identified, including in the budding yeast *S. cerevisiae* (termed "MIH1", Millar et al. (1991) *CSH, Symp. Quant. Biol.* 56:577), humans (Galaktinov et al. (1990) *Cell* 67:1181; and Sadhu et al. (1989) *PNAS* 87:5139), mouse (Kakizuka et al. (1992) *Genes Dev.* 6:578), Drosophila (Edgar et al. (1989) *Cell* 57:177; and Glover (1991) *Trends Genet.* 7:125), and *Xenopus* (Kumagai et al., (1992) *Cell* 70:139; and Jessus et al. (1992) *Cell* 68:323). Human cdc25 is encoded by a multi-gene family now consisting of at least three members, namely CDC25A (SEQ ID NO: 1), CDC25B (SEQ ID No. 2) and CDC25C (SEQ ID No. 3). It will be appreciated to those skilled in the art that the term "CDC25" as used herein does not include proteins related to the guanine nucleotide exchange factor of *S. cerevisiae* also called CDC25.

As stated above, the present invention facilitates the development of assays for identifying drugs which are either agonists or antagonists of the normal cellular function of a CDC25 phosphatase, or of the role of CDC25 phosphatases in the pathogenesis of abnormal cellular proliferation and/or differentiation and disorders related thereto, as mediated by Ras kinase-dependent activation of the phosphatase. In one embodiment, the assay evaluates the ability of a compound to modulate binding and/or enzymatic activation of a CDC25 phosphatase by a Raf kinase or other kinase of a ras-dependent signal cascade. A variety of assay formats will suffice and, in light of the present disclosure, those not expressly described herein will nevertheless be comprehended by one of ordinary skill in the art. Agents to be tested for their ability to act as CDC25 inhibitors can be produced, for example, by bacteria, yeast or other organisms (e.g. natural products), produced chemically (e.g. small molecules, including peptidomimetics), or produced recombinantly.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity between Raf proteins or in changes in an enzymatic property of the molecular target CDC25. Accordingly, in an exemplary screening assay of the present invention, the compound of interest is contacted with an isolated and purified Raf polypeptide which is ordinarily capable of binding a CDC25 protein, such a Raf protein comprising the CR3 domain. To the mixture of the compound and Raf polypeptide is then added a composition containing a CDC25 polypeptide. Detection and quantification of Raf/CDC25 complexes provides a means for determining the compound's efficacy at inhibiting (or potentiating) complex formation between the Raf and CDC25 polypeptides. The efficacy of the compound can be assessed by generating dose response curves from data obtained using various concentrations of the test compound. Moreover, a control assay can also be performed to provide a baseline for comparison. In the control assay, isolated and purified CDC25 polypeptide is added to a composition containing the Raf protein, and the formation of Raf/CDC25 complex is quantitated in the absence of the test compound. It will be understood that, in general, the order in which the reactants may be admixed can be varied, and can be admixed simultaneously.

Complex formation between the CDC25 polypeptide and Raf polypeptide may be detected by a variety of techniques. For instance, modulation of the formation of complexes can be quantitated using, for example, detectably labelled proteins such as radiolabelled (e.g. $^{32}$P, $^{35}$S, $^{14}$C or $^{3}$H), fluorescently labelled (e.g. FITC), or enzymatically labelled CDC25 or Raf polypeptides, by immunoassay, or by chromatographic detection. The use of enzymatically labeled proteins will, of course, generally be used only when enzymatically inactive portions of either CDC25 or Raf are used, as each protein can possess a measurable intrinsic activity which can be detected (described infra).

Typically, it will be desirable to immobilize either the Raf or the CDC25 polypeptide to facilitate separation of Raf/CDC25 complexes from uncomplexed forms of one or both of the proteins, as well as to accommodate automation of the assay. Binding and/or activation of the target CDC25 protein via a Raf protein, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/Raf (GST/Raf) fusion proteins can be adsorbed onto glutathione sepharose beads (Sigma Chemical, St. Louis, Mo.) or glutathione derivatized microtitre plates, which are then combined with the CDC25 polypeptide, e.g. an $^{35}$S-labeled CDC25 polypeptide, and the test compound, and the mixture incubated under conditions conducive to complex formation, e.g. at physiological conditions for salt and pH, though slightly more stringent conditions may be desired, e.g., at 4° C. in a buffer containing 0.6M NaCl or a detergent such as 0.1% Triton X-100. Following incubation, the beads are washed to remove any unbound CDC25 polypeptide, and the matrix immobilized radiolabel determined directly (e.g. beads placed in scintilant), or in the supernatant after the Raf/CDC25 complexes are subsequently dissociated. Alternatively, the complexes can dissociated from the matrix, separated by SDS-PAGE, and the level of CDC25 polypeptide found in the bead fraction quantitated from the gel using standard electrophoretic techniques such as described in the appended examples.

Other techniques for immobilizing proteins on matrices are also available for use in the subject assay. For instance, either of the Raf or CDC25 proteins can be immobilized utilizing conjugation of biotin and streptavidin. For instance, biotinylated Raf molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the Raf but which do not interfere with CDC25 binding can be derivatized to the wells of the plate, and the Raf trapped in the wells by antibody conjugation. As above, preparations of a CDC25 polypeptide and a test compound are incubated in the Raf-presenting wells of the plate, and the amount of Ras/CDC25 complex trapped in the well can be quantitated. Exemplary methods for detecting such complexes, in addition to those described above for the GST-immobilized complexes, include immunodetection of complexes using antibodies reactive with the CDC25 polypeptide, or which are reactive with the Raf protein and compete for binding with the CDC25 polypeptide; as well as enzyme-linked assays which rely on detecting an enzymatic activity associated with the CDC25 polypeptide (instead of the intrinsic activity). In the instance of the latter, the enzyme can be chemically conjugated or provided as a fusion protein with a CDC25 polypeptide. To illustrate, the (DC25 polypeptide can be chemically cross-linked or genetically fused with horseradish peroxidase, and the amount of CDC25 polypeptide trapped in the complex can be assessed with a chromogenic substrate of the enzyme, e.g. 3,3'-diamino-benzadine terahydrochloride or 4-chloro-1-napthol. Likewise, a fusion protein comprising the CDC25 polypeptide and glutathione-S-transferase can be provided, and complex formation quantitated by detecting the GST activity using 1-chloro-2,4-dinitrobenzene (Habig et al (1974) *J Biol Chem* 249:7130).

For processes which rely on immunodetection for quantitating one of the proteins trapped in the complex, antibodies against the protein, such as either of the anti-CDC25 or anti-Raf antibodies described herein, can be used. Alternatively, the protein to be detected in the complex can be "epitope tagged" in the form of a fusion protein which includes, in addition to the CDC25 polypeptide or Raf sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharamacia, N.J.).

Moreover, the subject assay can be generated to detect activation (or inactivation) of the phosphatase activity of a CDC25. Inhibitors (and potentiators) of Raf activation of CDC25 can be identified, for example, using assays as described above but which are particularly sensitive to detecting activation of the phosphatase activity of a CDC25 by a Raf kinase, rather than merely the binding of the two proteins. For example, the assay can be derived for detecting the catalytic conversion of a substrate by an activated CDC25 phosphatase. In an illustrative embodiment, a molecule or compound (e.g. a "test agent") to be assessed for its ability to inhibit Raf1-mediated activation of CDC25A or CDC25B is combined with the CDC25 enzyme, the Raf1 kinase, and a substrate of the CDC25 phosphatase activity. The resulting combination is maintained under conditions appropriate for the CDC25 enzyme to act upon the substrate if that enzyme is activated by the Ras1 kinase (e.g., see Examples 4 and 5 below). The conversion of the substrate to product by the subject CDC25 is assessed, and the result compared to the rate of conversion of the substrate in the absence of the test agent. A statistically significant decrease in the activity of the CDC25 phosphatase activity in the presence of the test agent, manifest as a decrease in rate of conversion of substrate to product relative to the same combination lacking the test agent, indicates that the test agent is an inhibitor of the Raf1 activation of CDC25. In addition to the equivalent assay system without the test agent, other suitable controls include formats where, in place of the Raf kinase, an activated CDK/cyclin (such as (CDC2/cyclinB) can be used. Such a control would be useful for distinguishing test agents which specifically inhibited Raf-dependent activation of CDC25, from agents which inhibit CDC25 itself or other CDC25 activators (such as a CDK/cyclin feedback loop).

In preferred embodiments, the substrate of the CDC25 tyrosine phosphatase is a synthetic substrate, e.g. a peptide or tyrosine analog, comprising a colorimetric label which is detectable when the substrate is catalytically acted upon by the CDC25. For instance, a preferred substrate is p-nitrophenylphosphate. Other substrates include radiolabeled peptides, such as peptides containing $^{32}$P-labeled phosphotyrosines, e.g. tyrosine phosphorylated forms of reduced carboxamindomethylated, maleyated lyzosyme (RCML) or CDC2-derived peptides, wherein release of the radiolabel can be detected and correlated with CDC25 enzymatic activity. In still further embodiments, phosphorylated CDK/cyclin complexes (e.g. inactive) can be provided and the activation of the CDK by CDC25-mediated dephosphorylation can be detected by measuring, for example, phosphorylation of histones by the activated CDK (or Rb where CDK4 or CDK6 are used). The ability of a test agent to inhibit the activation of the CDC25 enzyme is therefore manifest by a decrease in CDK activation as compared to the system in the absence of the test agent.

In an illustrative embodiment, the method comprises the steps of: (a) combining a compound to be assessed, a Ras kinase, a CDC25 phosphatase, such as from a mammal, and a synthetic substrate of the CDC25 tyrosine phosphatase activity which comprises a colorimetric label that is detectable when the substrate is acted upon by the CDC25 (e.g., p-nitrophenylphosphate); (b) maintaining the CDC25/Raf complex combination under conditions appropriate for an activated CDC25 to act upon the substrate; and (c) determining, by colorimetric assay, the extent to which the CDC25 enzyme present in the combination acted upon the substrate, relative to a control, the control comprising the Raf kinase, the CDC25 and the substrate. If the subject CDC25 enzyme acts upon the substrate to a lesser extent than in the control, the compound is an inhibitor of the CDC25 tyrosine phosphatase activity.

Other exemplary embodiments of assays which utilize detection of substrate conversion by CDC25 are provided in U.S. Pat. No. 5,294,538 and U.S. Pat. No. 5,441,880, and can be readily adapted for use in the subject assay by addition of a Raf kinase (and under appropriate conditions, e.g. reaction mixture includes ATP).

In exemplary embodiments of an in vitro assay, the CDC25/Raf system can be a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in Raf-mediated activation of CDC25, together with the (DC25 protein, are present in the mixture to at least 50% purity relative to all other proteins in the mixture, and more preferably are present at 90–95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure specific binding or activation of CDC25 by a Raf-dependent pathway (e.g. not by a CDK-dependent pathway).

Each of the protein components utilized to generate the reconstituted CDC25/Raf system are preferably isolated from, or otherwise substantially free of, other proteins normally associated with the proteins in a cell or cell lysate. The term "substantially free of other cellular proteins" (also referred to herein as "contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene, such as described in the attached examples. By "purified", it is meant, when referring to the component proteins preparations used to generate the reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above, "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. The term isolated as used herein also refers to a component protein that is substantially free of cellular material or culture medium when produced by recombinant DNA techniques, or chemical precursors or other chemicals when chemically synthesized.

As described in the examples provided below, the assay system can also be generated using cell lysates. In an exemplary embodiment, the cell lysates are derived from cells which over-express a recombinant form of at least one of CDC25 or a Ras kinase. For example, the cell lysates can be derived from yeast or insect cells which are caused to expression a recombinant form of one or both of the proteins of interest.

Moreover, it will be appreciated that, in light of the recent finding that Raf kinases are part of complexes that include other components of the MAP kinase family, the subject assay can be generated to include, in place of, or in addition to the Raf kinase, other proteins which bind to the Raf protein or which are down-stream targets of the Raf kinase activity, or which bind to the CDC25. For instance, the assays as described herein can be generated so that the Raf kinase has been replaced with a MAPK/ERK kinase (MEK) or a mitogen-activated protein kinase (MAPK). In another embodiment, the Raf kinase/CDC25 reaction mixture further includes a MEK, a MAPK or, alternatively, bcl1–2, and the activation of CDC25 or its involvement in protein-protein complexes with one or more of these proteins is detected in the presence and absence of a test compound.

In addition to the cell free systems, the present invention further contemplates cell-based and whole animal assays for identifying agents which affect the biological function of a Raf-mediated activation of CDC25. While these assay systems can certainly be used as primary screens for initial identification of compounds which alter the binding of the two proteins, the in vivo assays are more typically used as "secondary" screens for further accessing compounds identified in the primary screen (e.g., the "hits"). For example, in certain embodiments, secondary screens can be used to evaluate the ability of the agent to actually modulate the function of CDC25 in vivo, as well as to assess the cytotoxicity, bioavailability, and other pharmacokinetic parameters of the test compound.

In an exemplary cellular assay, the subject CDC25 and Raf proteins can be used to generate an interaction trap assay, as described in, for example: U.S. Pat. No: 5,283,173; PCT Publication WO 94/10300; Zervos et al. (1993) *Cell* 72:223–232; Madura et al. (1993) *J Biol Chem* 268:12046–12054; Bartel et al. (1993) *Biotechniques* 14:920–924, or Iwabuchi et al. (1993) *Oncogene* 8:1693–1696, for subsequently detecting agents which disrupt, or enhance, binding of a Rafprotein to a CDC25. In an illustrative embodiment, the interaction trap assay relies on reconstituting in vivo a functional transcriptional activator protein from two separate fusion proteins, one of which comprises the DNA-binding domain of a transcriptional activator fused to a CDC25 polypeptide. e.g. human CDC25A, CDC25B or CDC25C, preferably an enzymatically inactive mutant. The second fusion protein comprises a transcriptional activation domain (e.g. able to initiate RNA polymerase transcription) fused to one of at least a portion of a Raf protein able to bind the CDC25 polypeptide. When the Raf and CDC25 proteins interact, the two domains of the transcriptional activator protein are brought into sufficient proximity as to cause transcription of a reporter gene. The expression of that reporter gene, in the presence and absence of a test compound, is therefore useful to ascertain the ability of the test compound to affect the binding of the CDC25 and Raf proteins. Commercial kits for developing two-hybrid assays with the subject CDC25 Raf proteins are presently available (e.g., MATCHMAKER kit, ClonTech catalog number K1605-1, Palo Alto, Calif.).

In yet another embodiment, the a cell can be contacted with a test agent under conditions in which ras-mediated activation of CDC25 is induced in the cell, and the formation of complexes including a Ras kinase and a CDC25 phosphatase can be determined, for instance, by immunoblotting as described in Example 1. Alternatively, the level of activation of CDC25 can be detected as described, for example, by Dunphy et al. (199 1, *Cell* 67: 189–96). In general, such methods comprise the steps of providing a host cell expressing both a CDC25 phosphatase of interest and a Raf kinase, maintaining the cell under conditions wherein interactions between the Raf kinase and the CDC25 phosphatase occur, contacting the cell with a test agent, and detecting the formation of a Raf/CDC25 complex in the supernatant of a lysate from the cell, or detecting the level of phosphatase activity of the CDC25 phosphatase in a lysate prepared from the cell. Test agents which cause a statistically significant decrease in the level of Raf/CDC25 complexes, or in the enzymatic activity of the CDC25 phosphatase are likely to be inhibitors of Raf-dependent (and therefore ras-dependent) activation of CDC25.

In another embodiment, a cellular assay is provided identifying compounds which modulate ras-mediated activation of a CDC25 phosphatase based on detection of abnormal proliferative or growth characteristics. For instance, an exemplary embodiment comprises the steps of: a generating a host cell expressing a recombinant CDC25 phosphatase, and an oncogenic form of a ras protein or a kinase from a ras-mediated signal transduction cascade, which oncogenic protein phosphorylates the CDC25 phosphatase. Under these conditions, the host cell can manifest abnormal proliferation or growth characteristics due to activation of the CDC25 phosphatase by the oncogenic protein. Such characteristics can include hyper-proliferation of the cells, as well as cellular transformation, and may even result in cell death. The host cell can be contacted with a test agent to be assessed, and the proliferation or growth characteristics of the host cell which are dependent on the activation of the CDC25 phosphatase can be ascertained and compared to the same system in the absence of the test agent. For instance, the characteristics accompanying cellular transformation, such as increased capacity to persist in serial subcultures, growth in soft agar, increased growth rate in vitro, and/or loss of contact inhibition, can be assessed in the presence and absence of the test agent. A change in the CDC25-dependent proliferation or growth characteristics of the treated host cell, relative to the untreated host cell, indicates that the test agent is a modulator of ras-mediated activation of the CDC25 phosphatase. The host cell can be essentially any eukaryotic cell. In preferred embodiments, the host cell is a human cell, or a cell which recombinantly expresses one or both of a human CDC25 and a human Raf kinase. For instance, yeast and insect cells can be derived which been manipulated to express (in addition to, or in place of endogenous genes) human CDC25A or B and human Raf1 kinase. Suitable yeast expression vectors encoding each of these human proteins have been previously described (see, for example, Ruggieri et al. (1994) *Mol Biol Cell* 5:173–181, and Hughes et al (1993) *Nature* 364:349–352 for Raf1; and Galaktinov et al. (1991) *Cell* 67:1181 for CDC25A and B).

Yet another aspect of the invention pertains to methods of treating proliferative and/or differentiative disorders which arise from cells which, despite aberrant growth control, still require CDC25 for cell growth. There are a wide variety of pathological cell proliferative conditions for which modulating agents of Raf-mediated CDC25 activation can be use in treatment. For instance, agents identified in the assays of the present invention can provide therapeutic benefits, with the general strategy being the inhibition of an anomalous cell proliferation. For instance, the peptidomimetics or other small molecule inhibitors of a CDC25/Raf interaction can be used as a part of a treatment protocol in a cell in which signal transduction pathways upstream of the Rafprotein are dysfunctional. To illustrate, cell types which exhibit pathological or abnormal growth presumably dependent at least in part on a function of a CDC25 protein include various cancers and leukemias, psoriasis, bone diseases, fibroproliferative disorders such as involving connective tissues, atherosclerosis and other smooth muscle proliferative disorders, as well as chronic inflammation. In addition to proliferative disorders, the treatment of differentiative disorders which result from, for example, de-differentiation of tissue which may (optionally) be accompanied by abortive reentry into mitosis, e.g. mitosis. Such degenerative disorders include chronic neurodegenerative diseases of the nervous system, including Alzheimer's disease, Parkinson's disease, Huntington's chorea, amylotrophic lateral sclerosis and the like, as well as spinocerebellar degenerations. Other differentiative disorders include, for example, disorders associated with connective tissue, such as may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors. It will also be apparent that, by transient use of modulators of Raf-dependent activation of CDC25 (e.g. agonists and antagonists), in vivo reformation of tissue can be accomplished, e.g. in the development and maintenance of organs. By controlling the proliferative and differentiative potential for different cells, the subject gene constructs can be used to reform injured tissue, or to improve grafting and morphology of transplanted tissue. For instance, Raf/CDC25 agonists and antagonists can be employed in a differential manner to regulate different stages of organ repair after physical, chemical or pathological insult. For example, such regimens can be utilized in liver repair subsequent to a partial hepatectomy, or to promote regeneration of lung tissue in the treatment of emphysema.

For instance, as described in the Examples below, transformation of a cell can be due in part to oncogenic activation of a ras signal transduction pathway which activates a CDC25. Additionally, other data provided in the appended examples suggests that disorders susceptible to treatment with antagonists of Raf-mediated CDC25 activation include those arising from cells which are aberrantly stimulated by growth factors, such as through paracrine and autocrine mechanisms (though the latter may be considered an oncogenic activation of ras). Normal cell proliferation, for instance, is generally marked by responsiveness to positive autocrine or paracrine growth regulators, such as epidermal growth factor (EGF), platelet-derived growth factor (PDGF), vascular endothelial growth factor (VEGF), insulin, stem cell factor, macrophage colony-stimulating factor receptor interleukins, ciliary neurotrophic factor (CNTF), and Oncostatin-M. However, studies now implicate many different types of mitogens in various pathological proliferative disorders, and in the development of certain carcinomas. It is presently understood, for example, that many of the disease states which are characterized by the uncontrolled proliferation of cells involve a loss of control of normal autocrine or paracrine signaling. For example, such anomalous signaling frequently includes aberrant PDGF signals. These disease states involve a variety of cell types and include disorders such as leukemia, cancer, psoriasis, inflammatory diseases, bone diseases, atherosclerosis and restinosis occurring subsequent to angioplastic procedures.

To further illustrate the use of the subject method, the therapeutic application of an inhibitor of Raf-mediated activation of CDC25 can be used in the treatment of neuroglioimas. Gliomas account for 40–50% of intracranial tumors at all ages of life. Despite the increasing use of radiotherapy, chemotherapy, and sometimes immunotherapy after surgery for malignant glioma, the mortality and morbidity rates have not substantially improved. Furthermore, there is increasing experimental and clinical evidence that a significant number of human tumor cell lines, particularly those established from glioma and sarcoma, produce both growth factors and their cognate receptor. In these instances, tumor cell growth may be enhanced by an autocrine receptor activity which, by induction of ras signaling pathways, result in mitotic activation of CDC25. Accordingly, inhibition of Raf-mediated activation of a CDC25 phosphatase, which activation is an apparent consequence of growth factor stimulation, can be utilized to prevent autocrine-stimulated proliferation.

In another embodiment, the subject inhibitors of CDC25 activation can be used in the treatment of various sarcomas. Among the sarcomas, a strong correlation has been observed between mitogen expression (e.g. PDGF) and both increasing malignant tumor grade and increasing proliferating cell nuclear antigen index (Wang et al. (1994) *Cancer Res* 54:560–564). In a representative embodiment, an inhibitor of Raf1 phosphorylation of a CDC25 is used to treat certain breast cancers.

In similar fashion, therapeutic protocols involving delivery of such inhibitors can be used in the treatment of certain carcinomas. Human malignant melanoma, for example, serves as an model for progressive growth factor independence, with PDGF representing a likely candidate for persistent autocrine feedback loops.

This invention also provides a method of treating or preventing fibroproliferative disorders in which autocrine or paracrine signaling is implicated. For instance, the subject CDC25 modulatory agents can be used in the treatment of hyperproliferative vascular disorders, e.g. smooth muscle hyperplasia (such as atherosclerosis) or restinosis, as well as other disorders characterized by fibrosis, e.g. rheumatoid arthritis, insulin dependent diabetes mellitus, glomerulonephritis, cirrhosis, and scleroderma.

For example, restinosis continues to limit the efficacy of coronary angioplasty despite various mechanical and pharmaceutical interventions that have been employed. An important mechanism involved in the intimal proliferation of smooth muscle cells appears to be the induction of autocrine PDGF and/or VEGF loops in the smooth muscle cells. It may therefore be possible to treat or prevent restinosis by the use of agents which prevent activation of CDC25 by ras signal pathways.

Hepatic fibrosis, a consequence of most forms of chronic liver disease, is also believed to include PDGF autocrine pathways in the pathological progression of the disease. Accordingly, in one embodiment of the present invention, a inhibitor of the interaction between a Ras kinase and a CDC25 can be delivered to hepatocytic cells in order to reduce fibrotically-linked proliferation of hepatic cells.

Aberrant autocrine and paracrine signaling is also understood to play a significant role in local glomerular and interstitial sites in human kidney development and disease. For example, while growth factors may mediate proliferation and matrix deposition with constructive outcome of glomerulogenesis and vascularization, they may also contribute to destructive proliferation and sclerotic responses attending destructive glomerulopathies, such as glomerulonephritis, glomerulosclerosis, and diabetic nephropathy. For instance, mesangial cell proliferation, which is believed to be involved in the progressive accumulation of extracellular matrix components that reduce filtration by the kidney, is maintained by an autocrine mechanism involving upregulation of mesangial PDGF and PDGF receptors. Inhibition of PDGF-induced activation of CDC25 via an inhibitor of Ras kinase induction may therefore provide opportunities to arrest destructive renal processes. Consequently, the subject method provides a method of treating or inhibiting fibrotic glomerulopathies involving the in vivo delivery of the subject inhibitors to kidney tissue.

Recent evidence has also suggested the role of autocrine mechanisms in the pathogenesis of feline distemper. Therefore, in yet another embodiment of the present invention, inhibitors of Raf activation of CDC25 can be used as a part of a therapeutic protocol for the treatment of distemper, particularly feline distemper caused by feline sarcomavirus.

It has also become apparent that 20 to 30 percent of cancer disease is characterized by transformed cells expressing oncogenic products which are growth factor receptors or their mutated homologs, and which exhibit protein tyrosine kinase activity in the absence of exogenous stimulation. That is, they are capable of constitutive activation of signal transduction processes which drive the cell's proliferation. As in the case of autocrine regulation described above, inhibition of Raf-mediated activation of CDC25 by, for example, agents which disrupt the association of a Raf protein with a CDC25, can inhibit proliferation of tumor cells expressing oncogenic growth factor receptors, and accordingly may be used alone or for potentiating the efficacy of other chemotherapeutic agents.

More generally, it will be understood that agents which affect the ability of Raf kinases to activate CDC25 can be utilized to modulate the response of a cell to a growth factor or cytokine. For instance, sensitivity of a particular cell to a growth factor, or other mitogenic stimulus, which utilizes a ras signaling pathway can be either up-regulated or down-regulated by modulating the interactions of Raf and CDC25 proteins. For instance. inhibitors of Raf-mediated activation of CDC25 can be used to modulate an immune response, such as to cause general or specific immunosuppression. For instance, the compounds of the present invention can be used to prevent antigen-specific or mitogen-induced proliferation of B lymphocytes. Engagement of the B-cell antigen receptor complex induces immediate activation of receptor-associated Src family tyrosine kinases including p55blk, p59fyn, p53/56lyn, and perhaps p56lck. These kinases act directly or indirectly to phosphorylate and/or activate effector proteins including $p21^{ras}$, according to the present data, can induce mitotic progression by activation of CDC25. Accordingly, targeting such signal transduction pathways can result in inhibition of B-cell activation.

Likewise, another aspect of the present invention comprises the inhibition of T cell activation. Signal transduction through the T-cell receptor and cytokine receptors on the surface of T lymphocytes also includes ras-dependent pathways. Inhibition of T-cell activation by blocking ras-dependent activation of CDC25 may be used to effectively cause general clonal anergy.

In yet another embodiment, antagonists of ras-mediated activation of CDC25 can be used to inhibit spermatogenesis. Spermatogenesis is a process involving mitotic replication of a pool of diploid stem cells, followed by meiosis and terminal differentiation of haploid cells into morphologically and functionally polarized spermatoza. This process exhibits both temporal and spatial regulation, as well as coordinated interaction between the germ and somatic cells. It has been previously shown that the Raf kinases apparently play significant roles in coupling such extracellular stimulus to regulation of mitotic, meiotic events which occur during spermatogenesis (e.g., see Wadewitz et al. (1993) *Oncogene* 8:1055–1062; and Storm et al. (1990) *Oncogene* 5: 345–351). In light of the present findings demonstrating that Raf mediated activation of the meiotic and mitotic regulatory proteins, CDC25, it may be possible that antagonists of this activation can be utilized to block spermatogenesis and hence may be employed as male contraceptive agents.

Likewise, expression of Raf-kinases are required for meiotic maturation of oocytes (see, for example, Fabian et al. (1993) *J Cell Biol* 122:645–652. Accordingly, inhibitors generated in the subject assays can be used to prevent oocyte maturation and are therefore useful as contraceptives. Moreover, regulation of induction of meiotic maturation with such inhibitors can be used synchronize oocyte populations for in vitro fertilization. Such a protocol can be used to provide a more homogeneous population of oocytes which are healthier and more viable and more prone to cleavage, fertilization and development to blastocyst stage.

Moreover, it is further contemplated by the invention that compositions comprising agents which modulate the ability of Raf kinases to interact with and/or activate CDC25 can also be utilized in cell culture for generating and maintaining of tissue and cells. By manipulation of growth factor responses, including steps of inhibiting or potentiating CDC25 activation, tissue can be grown ex vivo to a desired differentiative state. That is, commitment of the cultured cells along a particular path, such as terminal differentiation, can be influenced by the effects of CDC25 activation, as for example, manifest by the phenotype of the cell as mitotic or post-mitotic. Accordingly, agents identified in the subject assays can be used, for example, in the ex vivo generation and maintenance of an artificial liver which can have multiple metabolic functions of a normal liver. In an exemplary embodiment, modulation of CDC25 activation by ras-signaling can be used, in conjunction with growth and differentiation factors, to facilitate differentiation of digestive tube stem cells to form hepatocyte cultures which can be used to populate extracellular matrices, or which can be encapsulated in biocompatible polymers, to form both implantable and extracorporeal artificial livers. The proliferative versus differentiative effect that various growth factors can have is controlled by regulating the activation of CDC25.

Similarly, therapeutic compositions containing such modulatory agents can be used to promote in vitro generation of lung tissue skeletal tissue such as from skeletogenic stem cells, as well as controlling differentiation and/or proliferation of chondrocytes embedded in prosthetic cartilage devices.

Moreover, inhibitors of the Raf/CDC25 interactions can be used in neuronal cell cultures to prevent proliferation of fibroblasts and/or glial cells induced by the use of growth factors in cultures differentiated neural tissue. For instance, anti-mitotic agents can be used in cultures of differentiated cells when proliferation of surrounding glial cells or astrocytes is undesirable in the regeneration of nerve cells which are being treated with growth factors which, while inducing differentiation of the nerve cells, are mitogenic to these supplemental cells.

The present invention also provides a means for immortalizing a wide range of cell types to produce cells which can retain the differentiated phenotypic characteristics of the parent cells.

In an exemplary embodiment, cells are contacted with expression vectors encoding. and caused to express, an oncogenic form of ras or a an oncogenic form of a protein involved in a ras signal transduction pathway and interposed between ras and a CDC25 phosphatase, e.g. a Raf kinase such as Raf1, A-Raf or B-Raf Cells expressing the oncogene are also caused to express a recombinant CDC25, such as CDC25A or CDC25B. As described in the examples below, CDC25 unexpectedly displays some oncogenic properties in mammalian cells, being able to cooperate with oncogenic ras in cellular transformation.

In an exemplary embodiment, epithelial cells which can be immortalized using the present method include those lining the respiratory, gastrointestinal, genitourinary and nervous systems. Examples of such epithelial cells include those of the oral and nasal mucosa, larnynx, trachea, lung, esophagus, stomach, duodenum, jejumin, ileum, and colon. Other epithelial cells which can be immortalized include liver, pancreas, kidney, bladder, adrenal and reproductive organ epithelium, such as cells obtained from the ovary, uterus (endometrium), testis and prostrate. Skin cells can also be immortalized by the method of the present invention, including hair follicle cells and dermal papillae which are necessary for hair follicle development.

In addition to epithelial cells, non-epithelial cells such as endothelial cells, fibroblasts, muscle cells, bone cells, cartilage cells and brain tissue cells (e.g. neurons, glial cells, etc.) can also be transformed/immortalized using the methods of the present invention. Further, hematopoietic cells, particularly progenitor cells, can be immortalized.

Cells which have been immortalized by the subject technique, particularly cells which have retained all or a substantial portion of their natural phenotype, are useful in a number of different manners. For instance, such cell cultures can be used in the generation of drug screening assays, as well as for toxicological studies, and can be employed in place of live animals.

Moreover, immortalized cells are also useful as a source of implantable tissue. For instance, cells which have a defective gene can be removed from a patient. The defective gene can be repaired by molecular biological techniques such that the correct gene product is expressed, and the genetically altered host cell then subjected to the subject method to generate an immortalized cell line expressing the desired product, preferably a non-tumorogenic cell line, which can be reintroduced into the patient.

In addition to standard techniques for introducing recombinant genes encoding each of the ras and CDC25 proteins, it will be understood that the one or both of the genes can be generated as nucleic acid constructs which are amenable to delivery by gene therapy techniques. For instance, expression constructs of the ras oncogene and CDC25 phosphatase may be administered in any biologically effective carrier, e.g. any formulation or composition capable of effectively delivering the genes to cells in vivo or in vitro as desired. Approaches include insertion of the genes in viral vectors including recombinant retroviruses, adenovirus, adeno-associated virus, and herpes simplex virus-1, or recombinant bacterial or eukaryotic plasmids. While viral vectors transfect cells directly, plasmid DNA can also be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of CDC25 and ras expression are also useful for in vitro transduction of cells, such as for use in the ex vivo tissue culture systems described above.

EXEMPLIFICATION

The invention now being generally described it will be more readily understood by reference to the following examples which are included merely for purposes of illustration of certain aspects and embodiments of the present invention, and are note intended to limit the invention.

As described below, we demonstrate that Raf1 kinase forms protein-protein complexes with the cell cycle activator, CDC25 phosphatase. This interaction was observed in human somatic cells and frog oocytes, and reconstructed in insect cells using recombinant proteins. Furthermore, bacterially produced human CDC25A and CDC25B were shown to associate with recombinant Raf1 produced in the insect cells. Binding of Ras1 to CDC25 depends on the C-terminal CR3 (kinase) domain of the Raf1 protein, a region indispensable for Raf1 transforming activity (Heidecker et al. (1990) *Mol. Cell Biol.* 10:2503–2512; and Stanton et al. (1989) *Mol. Cell Biol.* 9:639–647). Although we observed a strong interaction of Raf1 with human CDC25A and CDC25B, but not with CD(:25C, Raf1 also associates with Xenopus CDC25, which has been classified as a C-type 63. However, human CDC25C is 80aa shorter than Xenopus CDC25 protein and shares rather limited homology to it (Galaktionov et al. (1991) *Cell* 67:1181 –1194, and Kumagai et al. (1991) *Cell* 70:139–151).

The ability of Raf1 immunocomplexes to phosphorylate different human CDC25 proteins correlates with their Raf1-binding properties. This has also been shown for MEK, the only previously described substrate of Raf1 (Kyriakis, et al. (1992) *Nature* 358:417–421; Howe, et al. (1992) *Cell* 71:335–342; Dent, et al. (1992) *Science* 257:1404–1407, and vanAelst et al.(1993) *Proc. Natl. Acad. Sci. USA* 90:6213–6217). Raf1-dependent phosphorylation of CDC25A is associated with activation of phosphatase activity. We described here association of Raf1 with CDC25 and activation of the latter in a Raf1-dependent manner. It is quite possible that CDC25 is either phosphorylated directly by Raf1or by Raf1-dependent kinase that binds to the same protein complex. One candidate is MEK, but we can not exclude the possibility that a further uncharacterized kinase that is present in Hela and Sf9 cells binds to Raf1 and phosphorylates CDC25 proteins. In 3T3 cells, both activated Raf1 and MEK cause transformation or induction of the DNA replication in the latter case (Cowley, et al. (1994) *Cell* 77:841–852). The Raf1 kinase is an essential element of meiotic maturation, however, the downstream target of MEK, MAP kinase, is not involved in maturation in Xenopus oocytes, but is a part of CSF activity (Haccard, et al. (1993) *Science* 262:1262–1265). Therefore, we propose that at the level of Raf1 or MEK, mitogenic signal transduction pathways form a bifurcation with at least two major downstream targets: MAP kinases and CDC25 cell cycle phosphatases.

Membrane translocation of Raf1 has been recently shown to be important for its activation. We observed a small portion of Raf1/CDC25 complex being associated with a membrane/cytoskeletal fraction.

We present data on the oncogenic potential of the CDC25 proteins in the rodent cell assay. The CDC25A and B cooperate in foci formation with oncogenic Ha-ras, which by itself does not cause foci formation in this assay. Human CDC25C had no effect with or without Ras. We suggest that oncogenic Ras activates Raf1 kinase which brings about the activation of CDC25 phosphatases which, in increased abundance and in an activated state, in turn stimulate uncontrolled cell proliferation. Finally, the results presented here constitute the first direct link between cell cycle control and signal transduction pathways in higher eucaryotes.

EXAMPLE 1

CDC25A Associates with Raf1 in Human Cells

We first tested whether there might be a physical association between CDC25 and c-Raf1 in human tissue culture cells. Immunoprecipitates from human HeLa cell lysates, using antibody against the C-terminal peptide of human CDC25A protein, were blotted with antibodies against CDC25A or Raf1. Likewise, immunoprecipitates made with anti-Raf1 or anti-ras antibodies were reciprocally blotted with antibodies recognizing Raf1 or CDC25A. In each experiment, both CDC25A and Raf1 were detected in the reciprocal immune complexes. Specificity of the observed interactions was confirmed by the competition with antigenic peptides that eliminate any signal from blots performed with anti-CDC25A or Raf1 antibodies. Reciprocal immunoprecipitation was detected using both high and low stringency buffers. Immunoprecipitates with antibodies specific to CDC25A, CDC25B or CDC25C proteins indicated that the interaction was most clear between CDC25A and Raf1, but upon longer exposure, we could detect some interaction of Raf1 and CDC25B, but not with CDC25C. It was observed that the amount of Raf1 protein present in CDC25 immunocomplexes was somewhat greater than binding between Ras and Raf1, a well established interaction.

METHODS: Hela cells grown in suspension were obtained from Cold Spring Harbor Laboratory Tissue Culture Facility and used at the cell density $0.5–0.8 \times 10^6$ cells/ml. Cells were centrifuged for 10 min at 1000 g, washed with PBS three times and lysed in 5 volumes of the lysis buffer. In some experiments a standard buffer was used (Xiong et al. (1993) *Nature* 366:701–704). In other experiments, we used low ionic strengh buffer in the absence of NP40 (Galaktionov et al. (1991) *Cell* 67:1181 –1194). In these experiments, cells were swelled in this buffer for 5–10 minutes, followed by dounce homogenization or repeated passage through 26 gauge needle (5–6 times). Extracts were cleared from debris by centrifugation at 15000 g for 2x5 min at 4° C. Antibodies were raised against a peptide representing the eight C-terminal residues of the CDC25A (CMYSRLKKL) (SEQ ID No. 5) and another, representing seven C-terminal aminoacids of the CDC25B (CSRLQDQ) (SEQ ID No. 6). Both peptides were crosslinked with KLH and used to immunize rabbits. Antisera was collected and affinity purified using the peptides crosslinked with the Reacti-Gel(6x) beads (Pierce). GST-fusions with CDC25A, CDC25B and CDC25C were described previously (Galaktionov et al., supra), Proteins were purified as described (Galaktionov et al. supra) with slight modifications and used to immunize rabbits. Antisera against GST fusions were extensively depleted on GST-Sepharose beads followed by Sepharose beads with nonspecific CDC25 fusion GST-CDC25B was used to remove crossreacting species from anti-CDC25A antibodies, and vice-versa). Finally, specific antibodies were affinity purified using the relevant fusion protein attached to the Sepharose beads. We routinely used C-terminal peptide antibodies for immunoprecipitation, followed by western blotting with affinity purified antibodies against the full length protein. No cross-reactivities were detected between any of the affinity purified antibodies against CDC25A, CDC25B and CDC25C (both C-terminal and full length). Antibodies against C-terminus of the CDC25C have been described previously (Hoffmann et al. (1993) *EmboJ.* 12:53–63). Antibodies against Raf1 (C20) were purchased from Santa Cruz Biotechnology, Inc. All antibodies were used at ~0.5–1 ug per immunoprecipitation. Antibodies were typically incubated with cell extracts for 6–8 hours, followed by 1 hour incubation with protein A or protein G beads (Pierce, Pharmacia). Immunoprecipitates were recovered by low speed centrifugation, washed 4–5 times in the lysis buffer. Samples for 8.5% SDS-PAGE were prepared by treatment of the recovered immune complexes with sample buffer at 95° C. for 5–10 min as described (Laemmli, (1990) *Nature* 227:680–685). For immunoblotting analysis, proteins were transferred from the gels onto nitrocellulose, blocked with TBS/1% milk/0.1% Tween20 (TBSMT) for 30–45 min, incubated for 4–6 hours in the antibody solution (0.5 μg/ml in TBSMT), washed 3–4 times in TBS/0.25%BSA/0.1% Tween20 (TBSBT), incubated 60 min in 1:2000 dilution of Protein A-HRP (Amersham), washed 4–5 times (30 min total) in TBSBT, followed by a single TBS wash. Positive signals were detected using ECL (Amersham) according to instructions provided by the manufacturer.

Example 2

Interaction of Raf1 and (CDC25 proteins in vitro

Since Raf1 and CDC25A proteins appeared to interact in human cell extracts, we further investigated whether we could reconstruct this association using recombinant proteins expressed in insect cells. Thus, we coexpressed human Raf1 kinase (either wild type, kinase inactive mutant (K375NM) or an 'activated' allele (Y340D) (Fabian, et al. (1993) *Mol. Cell Biol.* 13:7170–7173) by co-infection with baculovirus expressing human CDC25A phosphatase. Extracts made from these cells were either directly probed with antibodies against Raf1 or CDC25A, or immunopecipitated with antibodies against CDC25A and then probed with anti-Raf1 antibodies. We detected a strong interaction between CDC25A and Raf1, The binding was similar among wild type Raf1 kinase, the kinase inactive mutant and the activated allele of Raf1. Similar results were obtained in a reciprocal experiment using immmunoprecipitations with anti-Raf1 and blotting with CDC25A antibodies.

To further confirm the specificity of the observed CDC25/Raf1 interaction, we assayed whether bacterially produced CDC25-glutathione-S transferase (GST) fusion protein could form complexes with Raf1 kinase. Extracts prepared from insect cells expressing various forms of Raf1 kinase were incubated with GST-CDC25A or GST alone and then recovered on glutathione agarose beads. The recovered material was probed with antibodies against Raf1. We observed binding of CDC25A to the wild type Raf1, the kinase inactive mutant of Raf1 (both K375M and interfering K375W), and Raf1 activated by triple transfection with Ras and src baculoviruses. Interestingly, an N-terminal deletion of 303 amino acid residues, producing a hyperactivated Raf1 kinase (22W) did not abolish interaction with CDC25A, indicating that CDC25 can associate with the carboxy-terminal kinase domain of the Ras1 protein (CR3).

We further determined the relative specificity of various human CDC25 proteins in their interaction with Raf1. Equivalent amounts of extracts from cells infected with Raf1 baculovirus were incubated with equal amounts of GST, GST-CDC25A, GST-CDC25B or GST-CDC25C proteins. Material recovered on glutathione beads was probed with anti-Raf1 antibody. The Raf1 kinase preferentially interacted with CDC25A, to a lesser extent with CDC25B, and vary weakly with CDC25C.

METHODS: *Spodoptera frugiperda* (Sf9) cells grown in monolayer were infected at 5× multiplicity with recombinant baculoviruses encoding CDC25A alone or in a combination with viruses encoding wild type Raf1, kinase inactive Raf1 (K375M or K375W), truncated Raf1 (22W) or 'activated' Raf1 (Y340D) (Fabian et al. supra, and Jessus et al. (1987) *J. Cell. Sci.* 87:705–712). In some cases triple transfection with Raf1, Ras and src baculoviruses were performed as previously described (Williams et al. (1992) *PNAS* 89:2922–2926). At 60–72 h post-infection, cells grown on 100 or 150 mm plates were washed with PBS, scraped from the plate, washed two more times in PBS and lysed in kinase buffer (KB), containing 25 mM HEPES, pH7.4,150 mM NaCl, 25 mM β-glycerophosphate, 10 mM $MgCl_2$, 0.1 mM EDTA, 5 mM EGTA, supplemented with 1 mM DTT, 1 mM o-vanadate. 10 μ/ml aprotinin, 10, ug/ml leupeptin, 0.5, ug/ml pepstatin, 1 μg/ml chymostatin,1 mM benzamidine, 0.5 mM PMSF. Cells were disrupted by passing 6 times through 261/2 gauge needle. Extracts were cleared by centrifugation twice at 15000 g for 15 min each. Cleared lysates were supplemented with glycerol to 20% and stored frozen at −70° C. in aliquots. Immunoprecipitations were done as described above. GST-fusion proteins and GST were purified as described (Galaktionov et al. supra) on a Glutathione Sepharose columns (Pharmacia) and eluted with 10 mM glutathione in GT buffer (50 mM Tris HCl , pH8.0, 200 mM NaCl,1 mM EDTA,10% glycerol, 1 mM DTT, supplemented with 0.5 mM PMSF, 1 mM benzamidine,10 μg/ml leupeptin,10 μg/ml aprotinin. GST or GST-fusion proteins were diluted at least 10 fold in KB, mixed with insect cell extracts (typically 2 μg of the GST fusion and 20–50 ul of the extract), and incubated on ice for 2–4 hours. Glutathione sepharose beads, equilibrated in KB buffer were added (30 μl of a 1:1 slurry), rotated at 4° C. for 1 hour and washed 4–5 times in KB. Samples were separated on 8.5% SDS-PAGE, electrotransferred onto nitrocellulose and probed with anti-Raf1 antibodies (0.2 μg/ml), followed by proteinA-HRP (1:2000–1:5000)(Amersham). Positive signals were detected using enhanced chemiluminescence (Amersham).

Example 3

Meiotic Raf1/CDC25 interaction to extend our observations on the interaction between CDC25 with Raf1, we took advantage of a well-defined biological system, namely Xenopus oocytes. Cytoplasmic extracts were prepared from prophase oocytes, progesterone-matured oocytes, eggs, activated by $Ca^2+$ in the presence of cycloheximide, cAMP-blocked oocytes and IGF-1-matured oocytes. The level of histone HI kinase activity in prophase, interphase and metaphase extracts was found to be as described previously (Labbe et al. (1988) Dev. Biol. 127:157–169). Similar extracts were probed with antibodies against Xenopus CDC25 (Kumagi et al. (1992) *Cell* 70:139–151) or anti- human Raf1 antibodies, which have been shown previously to crossreact with frog Raf1 (MacNicol et al. (1993) *Cell* 73:571–583). The relevant proteins were clearly detected. As described previously (Kumagi et al. supra), frog CDC25 undergoes a mobility shift from 70 to 90 kD apparent molecular weight in matured oocytes, and, at that same time, Raf1 has also been shown to alter its mobility to a slightly higher molecular weight (MacNicol et al., supra). To investigate potential Raf1/CDC25 interaction, equal amounts of extracts from interphase and activated oocytes and eggs were used for immunoprecipitations with anti-CDC.5 antibodies or anti-Raf1 antibodies and then blotted with anti-CDC25 antibodies or anti-Raf1 antibodies. A very significant reciprocal immunoprecipitation of Raf1 and CDC25 was observed. Interaction between Raf1 and CDC25 was detected in extracts prepared under each physiological condition. A Raf1/CDC25 complex was found largely in the supernatant following high speed (250000 g) clearing of the extracts, indicating that most of the complexes are soluble and cytoplasmic. A minor fraction of the CDC25 and Raf1 complex was present in a low speed pellet, suggesting presence of these proteins in the membrane/cytoskeletal fraction.

We further investigated the relative fraction of Xenopus CDC25 protein that exists in a complex with Raf1. Extracts prepared from prophase oocytes and progesterone-matured (metaphaseI II) oocytes were depleted with anti-Raf1 antibodies. The initial extracts, depleted extracts and immunoprecipitates were probed with anti-Raf1 or anti-CDC25 antibodies. Under these conditions Raf1 kinase was almost fully depleted from extracts, with the anti-Raf1 antibody resulting in a clear co-depletion (~75%) of CD25, indicating that the majority of the CD(25 molecules are present in the complex with Raf1. An 80kd protein, which represented a nonspecific peptide crossreacting with CDC25 antisera on Western blots, did not change in abundance following depletion with Ras i antibody, thus representing an internal control. Depleted Raf1 and CDC25 were retained in the Raf1 immunocomplexes. Raf1/CDC25 complex was found to be resistant to 1% NP40 or Triton X100 after completion of the immunoprecipitation, but sensitive to the addition of NP40 to the extracts before immunoprecipitates were performed. Specificity of the observed interaction was further confirmed by the absence of any significant binding between Raf1 and cyclin B2/CDC2. Some fraction of the CDC25 was shown to exist in a complex with cyclinB/CDC2 at the metaphase (Jessus et al. (1992) Cell 68:323–332). We suggest, however, that cyclinB/CDC2 could not bridge CDC25/Raf1 interaction for the reason that we observe equally strong interaction in prophase, metaphase and in activated eggs (interphase).

METHODS: Xenopus leavis prophase oocytes were prepared as described previously (Jessus et al., (1987) supra). Progesterone-induced meiotic maturation and egg activation were performed as described in (Jessus et al., (1992) supra), and IGF-1-induced meiotic maturation as described in (Jessus et al., (1989) supra). cAMP-blocked oocytes were pretreated for 1 h with 1 mM IBMX and 0.1 μg/ml cholera toxin before adding progesterone. Oocytes were rinsed extensively in extraction buffer EB (80 mM β-Glycerophosphate, 20 mM EGTA, 15 mM $MgCl_2$, 1 mM DTT, 25 mM NaF and 1 mM ortho-vanadate), then lysed in 5 vol of EB with protease inhibitors (1 mM PMSF, 25 μg/ml leupeptin, 25 μg/ml aprotinin, 1 mM benzamidine, 10 μg/ml TLCK and 70 μg/ml TPCK). Insoluble material and lipids were separated by centrifugation at 13,000 g for 15 min at 4° C. and the supernatant was used for immunoprecipitations and western blot analysis. Nitrocellulose filters were incubated for 4 h with primary antibody diluted in 1% milk-TBST. The carboxy-terminal antipeptide antibody (C-20, Santa Cruz Biotechnology, Inc.) and the anti-Xenopus CDC25 antibody (described in Kumagai et al. supra) were used at concentrations of 10 μg/10 ml and 2.5 μg/10 ml respectively. After washing, filters were incubated for 1 h with HRP-coupled protein A (Gibco) at a 1:5,000 dilution in 1% milk-TBST and developed using enhanced chemiluminescence (Amersham). Immunoprecipitations were performed by incubating oocyte lysates with the anti-Raf1 antibody (1 μg of C-20, Santa Cruz Biotechnology, Inc.) or with an anti-Xenopus CDC25 antibody (1:100 dilution; described in Izumi et al. (1992) J. Mol Biol 3: 927–939) for 4 h at 4° C. Protein A-Sepharose beads were used to collect the antigen-antibody complexes. To estimate CDC2 histone H1 kinase activity, immunoprecipitations were performed with an anti-Xenopus cyclin B2 antibody (dilution 1:100; described in Izumi et al. (1991) Mol Cell Biol 11:3860–3867) for 1 h at 4° C. Protein G-Sepharose beads were used to collect the antigen-antibody complexes; these were washed with kinase buffer and assayed for histone H1 kinase activity (Sadler et al. (1989) J. Biol Chem 264:856–861).

Example 4

Phosphorylation of CDC25 by Raf1-immunocomplexes

Since we observed in vivo and in vitro interaction between Raf1 and CDC25, we evaluated the potential significance of this phenomena with respect to phosphatase activity of human CDC25A. In initial experiments we used Raf1 immunoprecipitates from HeLa cells or from insect Sf9 cells coinfected with Raf1, Ras and src baculoviruses to yield maximally active Raf1 kinase (Williams et al. (1992) PNAS 89:2922–2926) and assayed kinase activity using GST-CDC25A as a substrate. Incorporation of the radioactive phosphate into the CDC25A fusion protein was observed, a reaction which was totally negated by competition with antigenic Raf1 peptide in the initial immunoprecipitation reaction. To address the specificity of phosphorylation with respect to different members of the CDC25 gene family, we assayed the ability of Raf1 immunoprecipitates from HeLa cells to phosphorylate equal amounts of GST, GST-CDC25A, GST-CDC25B, and GST-CDC25C. No phosphorylation of GST was detected. Phosphorylation of the CDC25A fusion protein was strong, followed by CDC25B, whereas the CDC25C protein was phosphorylated at least 100 times less efficiently than CDC25A.

METHODS: Immunoprecipitates of HeLa cell extracts with anti-Raf1 antibodies were done under standard conditions (Xiong et al. (1993) Nature 366:701–704). In some cases antigenic peptide was added at 2–3 μg/μg of antibody. Immunoprecipitates were washed twice in KB buffer and 1–2μg of GST or GST-fusion proteins were added. Reactions were supplemented with 50 μM ATP/1 μCi [$\gamma^{32}$p] ATP, incubated at 30° C. for 10 min and terminated by the addition of equal volume of the 2×Laemmli sample buffer. Proteins were resolved on 8.5% SDS-PAGE and phosphorylated products were detected by autoradiography at −70° C. on the Kodak X OMAT film.

Example 5

Raf-dependent Activation of CDC25A

To assess the effect of phosphorylation of CDC25A on its intrinsic phosphatase activity we incubated GST-CDC25A or GST with cell extracts from Sf9 cells expressing Raf1. After incubation with glutathione Sepharose beads, resulting complexes were washed, retaining Raf1 kinase associated with CDC25A, and then incubated in a kinase buffer (in the presence or absence of ATP). Thereafter, ATP was washed away and phosphatase activity was measured as previously described (Dunphy et al. (1991) Cell 67–189–196; and Galaktionov et al. supra) using the synthetic substrate paranitrophenylphosphate (PNPP). Three-four fold activation of the CDC25A phosphatase activity was detected. Activation was dependent upon addition of ATP, and was negligible with a kinase inactive Raf1 mutant.

METHODS: GST-CDC25A protein or GST were purified as described previously (Galaktionov et al., supra). Typically, 5–10 μg of CDC25A fusion or GST was incubated with 400–800 μl of the Raf1 (wild type or mutant) extracts for 4–8 hours at 4° C., followed by addition of 40 μl of glutathione-sepharose slurry (1:1) for an additional 1–2 hour incubation. Beads were washed four times with KB buffer, resuspended in 50 μl KB, ATPγS was added to 2 mM and samples were incubated for an additional 30 min. Beads were washed with cold phosphatase buffer (PB), containing 50 mM TrisHCl, pH8.0, 50 mm NaCl, 10 mM DTT and resuspended in PB, supplemented with 200 mM paranitrophenylphosphate (PNPP). Reaction mixtures were incubated at 30° C. for 15–30 min and phosphatase activity was assayed by measuring $OD_{410}$.

Example 6

Oncogenic potential of CDC25 PTPase

The interaction of human CDC25A and CDC25B with Raf1 and activation of CDC25A phosphatase activity by Raf1-dependent phosphorylation suggested that CDC25 might unexpectedly display some oncogenic properties in mammalian cells. To investigate this possibility we introduced CDC25A, B, and C in a mammalian expression vector under a constitutive promoter into normal mouse embryo fibroblasts at a very early passage, either alone or in combination with oncogenic versions of Ha-ras (G12V) or p53 (E258K). The cells were plated in either nonselective or selective (G418) media. After four weeks the plates were stained and photographed to detect formation of potentially transformed foci. There is strong foci forming cooperation between CDC25A and B and ocogenic Ha-ras (G12V), but no cooperation between CDC25C and Ras. A few weak foci were detected with CDC25A alone and only slightly more with CDC25A and mutant p53. Similar number of colonies were detected in every case after G418 selection. Morphological examination of the CDC25A/ras and CDC25B/ras foci showed a transformed cell morphology revealed by multilayer growth, loose attachment to the substrate and aneuploidy. No foci formation was observed with Ha-ras (G12V) alone. Cells from the individual foci were readily expanded in the presence of G418, demonstrating that they represent cells transfected with the plasmids rather than a spontaneously transformed mouse cells.

METHODS: Human CDC25A, 25B and 25C were subcloned into RcCMV or pcDNA3 vectors (Invitrogen). A plasmid with mutant p53 (E258K) expressed from the CMV promoter, and a plasmid (pNLV)-containing oncogenic c-Ha-ras (G12V) under control of LTR, as well as mouse (Balb/c) embryonic fibroblast cells were obtained at passage two were used to perform this experiment. Cells were split 1:4 every 2–3 days. Cells were were transfected at passage using standard calcium phosphate precipitates (24–48 hours after split). Precipitates (from 20µg of plasmid(s)) were incubated with cells for 12–14 hours. Cells were washed with PBS, glycerol shocked, washed in PBS three times and recovered in complete media for 24 hours before splitting 1:4 on selective (G418) or non selective media. In the latter case cells were fed once every 4 days and after 4–5 weeks stained with 0.4% crystal violet in 20% ethanol.

All of the above-cited references and publications are hereby incorporated by reference.

Equivalents

Those skilled in the art will recognize, or be able to ascertain using no more than routine experimentation, numerous equivalents to the specific assay and reagents described herein. Such equivalents are considered to be within the scope of this invention and are covered by the following claims.

We claim:

1. A method for identifying a compound which is an inhibitor of ras-mediated activation of a CDC25 phosphatase, comprising the steps of:
   a) generating a reconstituted protein combination including:
      1) a test agent to be assessed;
      2) a purified protein preparation of a mammalian CDC25 phosphatase,
      3) a purified protein preparation of a kinase from a ras-mediated signal transduction cascade, which kinase phosphorylates the CDC25 phosphatase; and
      4) a substrate of the CDC25 phosphatase;
   b) maintaining the combination under conditions appropriate for the kinase to phosphorylate the CDC25 phosphatase and for an activated CDC25 phosphatase to convert the substrate to product; and
   c) measuring the conversion of the substrate to product, wherein a decrease in the conversion of substrate to product in the combination, relative to a control comprising the CDC25 phosphatase, the kinase, and the substrate and lacking the test agent, indicates that the test compound is an inhibitor of ras-mediated activation of the CDC25 phosphatase.

2. The method of claim 1, wherein the kinase is a Raf kinase.

3. The method of claim 2, wherein the Raf kinase is a Raf-1 kinase.

4. The method of claim 1, wherein the kinase is selected from the group consisting of a MAPK/ERK kinase (MEK), a mitogen-activated protein kinase (MAPK), and a MAP kinase (ERK).

5. The method of claim 1, wherein the CDC25 phosphatase is selected from the group consisting of CDC25A, CDC25B, and CDC25C.

6. The method of claim 1, wherein one or both of the CDC25 phosphatase and the kinase are fusion proteins.

7. The method of claim 6, wherein the fusion protein is a glutathione-S-transferase fusion protein.

8. The method of claim 1, wherein the conversion of substrate to product provides a colorimetric indicator of phosphatase activity.

9. The method of claim 8, wherein the substrate of the CDC25 phosphatase comprises a p-nitrophenylphosphate.

10. The method of claim 1, wherein the substrate of the CDC25 phosphatase comprises an inactive CDK/cyclin complex.

11. The method of claim 1, wherein the CDC25 phosphatase comprises the amino acid sequence encoded by nucleotide residues 460–2031 of SEQ ID No. 1, nucleotide residues 73–1773 of SEQ ID No. 2, or nucleotide residues 211–1631 of SEQ ID No. 3, or a fragment thereof which binds to the kinase and converts the substrate to product.

12. The method of claim 1, wherein the kinase comprises the amino acid sequence encoded by nucleotide residues 130–2073 of SEQ ID No. 4, or a fragment thereof which binds to the kinase and converts the substrate to product.

13. The method of claim 1, wherein the CDC25 phosphatase is a CDC25A phosphatase.

14. The method of claim 1, wherein the CDC25 phosphatase is a CDC25B phosphatase.

15. The method of claim 1, wherein the CDC25 phosphatase is a CDC25C phosphatase.

16. The method of claim 1, wherein the CDC25 phosphatase is a human CDC25A phosphatase.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2420 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 460..2031

(xi) SEQUENCE DESCRIPTION: SEQ ID NO:1:

```
CGAAAGGCCG GCCTTGGCTG CGACAGCCTG GGTAAGAGGT GTAGGTCGGC TTGGTTTTCT      60

GCTACCCGGA GCTGGGCAAG CGGGTGGGGA GAACAGCGAA GACAGCGTGA GCCTGGGCCG     120

TTGCCTCGAG GCTCTCGCCC GGCTTCTCTT GCCGACCCGC CACGTTTGTT TGGATTTAAT     180

CTTACAGCTG GTTGCCGGCG CCCGCCCGCC CGCTGGCCTC GCGGTGTGAG AGGGAAGCAC     240

CCGTGCCTGT GTCTCGTGGC TGGCGCCTGG AGGGTCCGCA CACCCGCGCG GCCGCGCCGC     300

TTTGCCCGCG GCAGCCGCGT CCCTGAACCG CGGAGTCGTG TTTGTGTTTG ACCCGCGGGC     360

GCCGGTGGCG CGCGGCCGAG GCCGGTGTCG GCGGGGCGGG GCGGTCGCGC GGGAGGCAGA     420

GGAAGAGGGA GCGGGAGCTC TGCGAGGCCG GGCGCCGCC ATG GAA CTG GGC CCG       474
```

```
                                          Met Glu Leu Gly Pro
                                            1               5

AGC CCC GCA CCG CGC CGC CTG CTC TTC GCC TGC AGC CCC CCT CCC GCG    522
Ser Pro Ala Pro Arg Arg Leu Leu Phe Ala Cys Ser Pro Pro Pro Ala
             10                  15                  20

TCG CAG CCC GTC GTG AAG GCG CTA TTT GGC GCT TCA GCC GCC GGG GGA    570
Ser Gln Pro Val Val Lys Ala Leu Phe Gly Ala Ser Ala Ala Gly Gly
                 25                  30                  35

CTG TCG CCT GTC ACC AAC CTG ACC GTC ACT ATG GAC CAG CTG CAG GGT    618
Leu Ser Pro Val Thr Asn Leu Thr Val Thr Met Asp Gln Leu Gln Gly
             40                  45                  50

CTG GGC AGT GAT TAT GAG CAA CCA CTG GAG GTG AAG AAC AAC AGT AAT    666
Leu Gly Ser Asp Tyr Glu Gln Pro Leu Glu Val Lys Asn Asn Ser Asn
         55                  60                  65

CTG CAG ATA ATG GGC TCC TCC AGA TCA ACA GAT TCA GGT TTC TGT CTA    714
Leu Gln Ile Met Gly Ser Ser Arg Ser Thr Asp Ser Gly Phe Cys Leu
 70                  75                  80                  85

GAT TCT CCT GGG CCA TTG GAC AGT AAA GAA AAC CTT GAA AAT CCT ATG    762
Asp Ser Pro Gly Pro Leu Asp Ser Lys Glu Asn Leu Glu Asn Pro Met
                 90                  95                 100

AGA AGA ATA CAT TCC CTA CCT CAA AAG CTG TTG GGA TGT AGT CCA GCT    810
Arg Arg Ile His Ser Leu Pro Gln Lys Leu Leu Gly Cys Ser Pro Ala
             105                 110                 115

CTG AAG AGG AGC CAT TCT GAT TCT CTT GAC CAT GAC ATC TTT CAG CTC    858
Leu Lys Arg Ser His Ser Asp Ser Leu Asp His Asp Ile Phe Gln Leu
         120                 125                 130

ATC GAC CCA GAT GAG AAC AAG GAA AAT GAA GCC TTT GAG TTT AAG AAG    906
Ile Asp Pro Asp Glu Asn Lys Glu Asn Glu Ala Phe Glu Phe Lys Lys
     135                 140                 145

CCA GTA AGA CCT GTA TCT CGT GGC TGC CTG CAC TCT CAT GGA CTC CAG    954
Pro Val Arg Pro Val Ser Arg Gly Cys Leu His Ser His Gly Leu Gln
150                 155                 160                 165

GAG GGT AAA GAT CTC TTC ACA CAG AGG CAG AAC TCT GCC CAG CTC GGA   1002
Glu Gly Lys Asp Leu Phe Thr Gln Arg Gln Asn Ser Ala Gln Leu Gly
                 170                 175                 180

ATG CTT TCC TCA AAT GAA AGA GAT AGC AGT GAA CCA GGG AAT TTC ATT   1050
Met Leu Ser Ser Asn Glu Arg Asp Ser Ser Glu Pro Gly Asn Phe Ile
             185                 190                 195

CCT CTT TTT ACA CCC CAG TCA CCT GTG ACA GCC ACT TTG TCT GAT GAG   1098
Pro Leu Phe Thr Pro Gln Ser Pro Val Thr Ala Thr Leu Ser Asp Glu
         200                 205                 210

GAT GAT GGC TTC GTG GAC CTT CTC GAT GGA GAC AAT CTG AAG AAT GAG   1146
Asp Asp Gly Phe Val Asp Leu Leu Asp Gly Asp Asn Leu Lys Asn Glu
     215                 220                 225

GAG GAG ACC CCC TCG TGC ATG GCA AGC CTC TGG ACA GCT CCT CTC GTC   1194
Glu Glu Thr Pro Ser Cys Met Ala Ser Leu Trp Thr Ala Pro Leu Val
230                 235                 240                 245

ATG AGA ACT ACA AAC CTT GAC AAC CGA TGC AAG CTG TTT GAC TCC CCT   1242
Met Arg Thr Thr Asn Leu Asp Asn Arg Cys Lys Leu Phe Asp Ser Pro
                 250                 255                 260

TCC CTG TGT AGC TCC AGC ACT CGG TCA GTG TTG AAG AGA CCA GAA CGT   1290
Ser Leu Cys Ser Ser Ser Thr Arg Ser Val Leu Lys Arg Pro Glu Arg
             265                 270                 275

TCT CAA GAG GAG TCT CCA CCT GGA AGT ACA AAG AGG AGG AAG AGC ATG   1338
Ser Gln Glu Glu Ser Pro Pro Gly Ser Thr Lys Arg Arg Lys Ser Met
         280                 285                 290

TCT GGG GCC AGC CCC AAA GAG TCA ACT AAT CCA GAG AAG GCC CAT GAG   1386
Ser Gly Ala Ser Pro Lys Glu Ser Thr Asn Pro Glu Lys Ala His Glu
     295                 300                 305
```

-continued

```
ACT CTT CAT CAG TCT TTA TCC CTG GCA TCT TCC CCC AAA GGA ACC ATT      1434
Thr Leu His Gln Ser Leu Ser Leu Ala Ser Ser Pro Lys Gly Thr Ile
310                 315                 320                 325

GAG AAC ATT TTG GAC AAT GAC CCA AGG GAC CTT ATA GGA GAC TTC TCC      1482
Glu Asn Ile Leu Asp Asn Asp Pro Arg Asp Leu Ile Gly Asp Phe Ser
            330                 335                 340

AAG GGT TAT CTC TTT CAT ACA GTT GCT GGG AAA CAT CAG GAT TTA AAA      1530
Lys Gly Tyr Leu Phe His Thr Val Ala Gly Lys His Gln Asp Leu Lys
                345                 350                 355

TAC ATC TCT CCA GAA ATT ATG GCA TCT GTT TTG AAT GGC AAG TTT GCC      1578
Tyr Ile Ser Pro Glu Ile Met Ala Ser Val Leu Asn Gly Lys Phe Ala
        360                 365                 370

AAC CTC ATT AAA GAG TTT GTT ATC ATC GAC TGT CGA TAC CCA TAT GAA      1626
Asn Leu Ile Lys Glu Phe Val Ile Ile Asp Cys Arg Tyr Pro Tyr Glu
    375                 380                 385

TAC GAG GGA GGC CAC ATC AAG GGT GCA GTG AAC TTG CAC ATG GAA GAA      1674
Tyr Glu Gly Gly His Ile Lys Gly Ala Val Asn Leu His Met Glu Glu
390                 395                 400                 405

GAG GTT GAA GAC TTC TTA TTG AAG AAG CCC ATT GTA CCT ACT GAT GGC      1722
Glu Val Glu Asp Phe Leu Leu Lys Lys Pro Ile Val Pro Thr Asp Gly
            410                 415                 420

AAG CGT GTC ATT GTT GTG TTT CAC TGC GAG TTT TCT TCT GAG AGA GGT      1770
Lys Arg Val Ile Val Val Phe His Cys Glu Phe Ser Ser Glu Arg Gly
                425                 430                 435

CCC CGC ATG TGC CGG TAT GTG AGA GAG AGA GAT CGC CTG GGT AAT GAA      1818
Pro Arg Met Cys Arg Tyr Val Arg Glu Arg Asp Arg Leu Gly Asn Glu
        440                 445                 450

TAC CCC AAA CTC CAC TAC CCT GAG CTG TAT GTC CTG AAG GGG GGA TAC      1866
Tyr Pro Lys Leu His Tyr Pro Glu Leu Tyr Val Leu Lys Gly Gly Tyr
    455                 460                 465

AAG GAG TTC TTT ATG AAA TGC CAG TCT TAC TGT GAG CCC CCT AGC TAC      1914
Lys Glu Phe Phe Met Lys Cys Gln Ser Tyr Cys Glu Pro Pro Ser Tyr
470                 475                 480                 485

CGG CCC ATG CAC CAC GAG GAC TTT AAA GAA GAC CTG AAG AAG TTC CGC      1962
Arg Pro Met His His Glu Asp Phe Lys Glu Asp Leu Lys Lys Phe Arg
            490                 495                 500

ACC AAG AGC CGG ACC TGG GCA GGG GAG AAG AGC AAG AGG GAG ATC TAC      2010
Thr Lys Ser Arg Thr Trp Ala Gly Glu Lys Ser Lys Arg Glu Ile Tyr
                505                 510                 515

AGT CGT CTG AAG AAG CTC TGAGGCGGC AGGACCAGCC AGCAGCAGCC              2058
Ser Arg Leu Lys Lys Leu
            520

CAAGCTTCCC TCCATCCCCC TTTACCCTCT TTCCTGCAGA GAAACTTAAG CAAAGGGGAC    2118

AGCTGTGTGA CATTTGGAGA GGGGGCCTGG GACTTCCATG CCTTAAACCT ACCTCCCACA    2178

CTCCCAAGGT TGGAGACCCA GGCCATCTTG CTGGCTACGC CTCTTCTGTC CCTGTTAGAC    2238

GTCCTCCGTC CATTACAGAA CTGTGCCACA ATGCAGTTCT GAGCACCGTG TCAAGCTGCT    2298

CTGAGCCACA GTGGGATGAA CCAGCCGGGG CCTTATCGGG CTCCAGCATC TCATGAGGGG    2358

AGAGGAGACG GAGGGGACTA GAGAAGTTTA CACAGAAATG CTGCTGGCCA AATAGCAAAG    2418

AG                                                                  2420
```

(2) INFORMATION FOR SEQ ID NO:2:

(i) SEQUENCE CHARACTERISTICS:
        (A) LENGTH: 2886 base pairs
        (B) TYPE: nucleic acid
        (C) STRANDEDNESS: single
        (D) TOPOLOGY: linear -continued (ii) MOLECULE TYPE: cDNA (ix) FEATURE:
    (A) NAME/KEY: CDS
    (B) LOCATION: 73..1773

(xi) SEQUENCE DESCRIPTION: SEQ ID NO:2:

```
CTGCCCTGCG CCCCGCCCTC CAGCCAGCCT GCCAGCTGTG CCGGCGTTTG TTGGTCTGCC            60

GGCCCCGCCG CG ATG GAG GTG CCC CAG CCG GAG CCC GCG CCA GGC TCG              108
              Met Glu Val Pro Gln Pro Glu Pro Ala Pro Gly Ser
                1               5                  10

GCT CTC AGT CCA GCA GGC GTG TGC GGT GGC GCC CAG CGT CCG GGC CAC            156
Ala Leu Ser Pro Ala Gly Val Cys Gly Gly Ala Gln Arg Pro Gly His
         15                  20                  25

CTC CCG GGC CTC CTG CTG GGA TCT CAT GGC CTC CTG GGG TCC CCG GTG            204
Leu Pro Gly Leu Leu Leu Gly Ser His Gly Leu Leu Gly Ser Pro Val
     30                  35                  40

CGG GCG GCC GCT TCC TCG CCG GTC ACC ACC CTC ACC CAG ACC ATG CAC            252
Arg Ala Ala Ala Ser Ser Pro Val Thr Thr Leu Thr Gln Thr Met His
 45                  50                  55                  60

GAC CTC GCC GGG CTC GGC AGC CGC AGC CGC CTG ACG CAC CTA TCC CTG            300
Asp Leu Ala Gly Leu Gly Ser Arg Ser Arg Leu Thr His Leu Ser Leu
                 65                  70                  75

TCT CGA CGG GCA TCC GAA TCC TCC CTG TCG TCT GAA TCC TCC GAA TCT            348
Ser Arg Arg Ala Ser Glu Ser Ser Leu Ser Ser Glu Ser Ser Glu Ser
             80                  85                  90

TCT GAT GCA GCT CTC TGC ATG GAT TCC CCC AGC CCT CTG GAC CCC CAC            396
Ser Asp Ala Ala Leu Cys Met Asp Ser Pro Ser Pro Leu Asp Pro His
         95                 100                 105

ATG GCG GAG CAG ACG TTT GAA CAG GCC ATC CAG GCA GCC AGC CGG ATC            444
Met Ala Glu Gln Thr Phe Glu Gln Ala Ile Gln Ala Ala Ser Arg Ile
    110                 115                 120

ATT CGA AAC GAG CAG TTT GCC ATC AGA CGC TTC CAG TCT ATG CCG GTG            492
Ile Arg Asn Glu Gln Phe Ala Ile Arg Arg Phe Gln Ser Met Pro Val
125                 130                 135                 140

AGG CTG CTG GGC CAC AGC CCC GTG CTT CGG AAC ATC ACC AAC TCC CAG            540
Arg Leu Leu Gly His Ser Pro Val Leu Arg Asn Ile Thr Asn Ser Gln
                145                 150                 155

GCG CCC GAC GGC CGG AGG AAG AGC GAG GCG GGC AGT GGA GCT GCC AGC            588
Ala Pro Asp Gly Arg Arg Lys Ser Glu Ala Gly Ser Gly Ala Ala Ser
            160                 165                 170

AGC TCT GGG GAA GAC AAG GAG AAT GAT GGA TTT GTC TTC AAG ATG CCA            636
Ser Ser Gly Glu Asp Lys Glu Asn Asp Gly Phe Val Phe Lys Met Pro
        175                 180                 185

TGG AAC CCC ACA CAT CCC AGC TCC ACC CAT GCT CTG GCA GAG TGG GCC            684
Trp Asn Pro Thr His Pro Ser Ser Thr His Ala Leu Ala Glu Trp Ala
    190                 195                 200

AGC CGC AGG GAA GCC TTT GCC CAG AGA CCC AGC TCG GCC CCC GAC CTG            732
Ser Arg Arg Glu Ala Phe Ala Gln Arg Pro Ser Ser Ala Pro Asp Leu
205                 210                 215                 220

ATG TGT CTC AGT CCT GAC CCG AAG ATG GAA TTG GAG GAG CTC AGC CCC            780
Met Cys Leu Ser Pro Asp Pro Lys Met Glu Leu Glu Glu Leu Ser Pro
                225                 230                 235

CTG GCC CTA GGT CGC TTC TCT CTG ACC CCT GCA GAG GGG GAT ACT GAG            828
Leu Ala Leu Gly Arg Phe Ser Leu Thr Pro Ala Glu Gly Asp Thr Glu
            240                 245                 250

GAA GAT GAT GGA TTT GTG GAC ATC CTA GAG AGT GAC TTA AAG GAT GAT            876
Glu Asp Asp Gly Phe Val Asp Ile Leu Glu Ser Asp Leu Lys Asp Asp
        255                 260                 265

GAT GCA GTT CCC CCA GGC ATG GAG AGT CTC ATT AGT GCC CCA CTG GTC            924
```

-continued

```
Asp Ala Val Pro Pro Gly Met Glu Ser Leu Ile Ser Ala Pro Leu Val
            270                 275                 280

AAG ACC TTG GAA AAG GAA GAG GAA AAG GAC CTC GTC ATG TAC AGC AAG       972
Lys Thr Leu Glu Lys Glu Glu Glu Lys Asp Leu Val Met Tyr Ser Lys
285                 290                 295                 300

TGC CAG CGG CTC TTC CGC TCT CCG TCC ATG CCC TGC AGC GTG ATC CGG      1020
Cys Gln Arg Leu Phe Arg Ser Pro Ser Met Pro Cys Ser Val Ile Arg
                    305                 310                 315

CCC ATC CTC AAG AGG CTG GAG CGG CCC CAG GAC AGG GAC ACG CCC GTG      1068
Pro Ile Leu Lys Arg Leu Glu Arg Pro Gln Asp Arg Asp Thr Pro Val
                320                 325                 330

CAG AAT AAG CGG AGG CGG AGC GTG ACC CCT CCT GAG GAG CAG CAG GAG      1116
Gln Asn Lys Arg Arg Arg Ser Val Thr Pro Pro Glu Glu Gln Gln Glu
            335                 340                 345

GCT GAG GAA CCT AAA GCC CGC GCT CTC CGC TCA AAA TCA CTG TGT CAC      1164
Ala Glu Glu Pro Lys Ala Arg Ala Leu Arg Ser Lys Ser Leu Cys His
350                 355                 360

GAT GAG ATC GAG AAC CTC CTG GAC AGT GAC CAC CGA GAG CTG ATT GGA      1212
Asp Glu Ile Glu Asn Leu Leu Asp Ser Asp His Arg Glu Leu Ile Gly
365                 370                 375                 380

GAT TAC TCT AAG GCC TTC CTC CTA CAG ACA GTA GAC GGA AAG CAC CAA      1260
Asp Tyr Ser Lys Ala Phe Leu Leu Gln Thr Val Asp Gly Lys His Gln
                    385                 390                 395

GAC CTC AAG TAC ATC TCA CCA GAA ACG ATG GTG GCC CTA TTG ACG GGC      1308
Asp Leu Lys Tyr Ile Ser Pro Glu Thr Met Val Ala Leu Leu Thr Gly
                400                 405                 410

AAG TTC AGC AAC ATC GTG GAT AAG TTT GTG ATT GTA GAC TGC AGA TAC      1356
Lys Phe Ser Asn Ile Val Asp Lys Phe Val Ile Val Asp Cys Arg Tyr
            415                 420                 425

CCC TAT GAA TAT GAA GGC GGG CAC ATC AAG ACT GCG GTG AAC TTG CCC      1404
Pro Tyr Glu Tyr Glu Gly Gly His Ile Lys Thr Ala Val Asn Leu Pro
430                 435                 440

CTG GAA CGC GAC GCC GAG AGC TTC CTA CTG AAG AGC CCC ATC GCG CCC      1452
Leu Glu Arg Asp Ala Glu Ser Phe Leu Leu Lys Ser Pro Ile Ala Pro
445                 450                 455                 460

TGT AGC CTG GAC AAG AGA GTC ATC CTC ATT TTC CAC TGT GAA TTC TCA      1500
Cys Ser Leu Asp Lys Arg Val Ile Leu Ile Phe His Cys Glu Phe Ser
                    465                 470                 475

TCT GAG CGT GGG CCC CGC ATG TGC CGT TTC ATC AGG GAA CGA GAC CGT      1548
Ser Glu Arg Gly Pro Arg Met Cys Arg Phe Ile Arg Glu Arg Asp Arg
                480                 485                 490

GCT GTC AAC GAC TAC CCC AGC CTC TAC TAC CCT GAG ATG TAT ATC CTG      1596
Ala Val Asn Asp Tyr Pro Ser Leu Tyr Tyr Pro Glu Met Tyr Ile Leu
            495                 500                 505

AAA GGC GGC TAC AAG GAG TTC TTC CCT CAG CAC CCG AAC TTC TGT GAA      1644
Lys Gly Gly Tyr Lys Glu Phe Phe Pro Gln His Pro Asn Phe Cys Glu
510                 515                 520

CCC CAG GAC TAC CGG CCC ATG AAC CAC GAG GCC TTC AAG GAT GAG CTA      1692
Pro Gln Asp Tyr Arg Pro Met Asn His Glu Ala Phe Lys Asp Glu Leu
525                 530                 535                 540

AAG ACC TTC CGC CTC AAG ACT CGC AGC TGG GCT GGG GAG CGG AGC CGG      1740
Lys Thr Phe Arg Leu Lys Thr Arg Ser Trp Ala Gly Glu Arg Ser Arg
                    545                 550                 555

CGG GAG CTC TGT AGC CGG CTG CAG GAC CAG TGAGGGGCCT GCGCCAGTCC        1790
Arg Glu Leu Cys Ser Arg Leu Gln Asp Gln
                560                 565

TGCTACCTCC CTTGCCTTTC GAGGCCTGAA GCCAGCTGCC CTATGGGCCT GCCGGGCTGA    1850

GGGCCTGCTG GAGGCCTCAG GTGCTGTCCA TGGGAAAGAT GGTGTGGTGT CCTGCCTGTC    1910
```

-continued

```
TGCCCCAGCC CAGATTCCCC TGTGTCATCC CATCATTTTC CATATCCTGG TGCCCCCCAC    1970

CCCTGGAAGA GCCCAGTCTG TTGAGTTAGT TAAGTTGGGT TAATACCAGC TTAAAGTCAG    2030

TATTTTGTGT CCTCCAGGAG CTTCTTGTTT CCTTGTTAGG GTTAACCCTT CATCTTCCTG    2090

TGTCCTGAAA CGCTCCAGAG CTAAACTCCT TCCTGGCCTG AGAGTCAGCT CTCTGCCCTG    2150

TGTACTTCCC GGGCCAGGGC TGCCCCTAAT CTCTGTAGGA ACCGTGGTAT GTCTGCCATG    2210

TTGCCCCTTT CTCTTTTCCC CTTTCCTGTC CCACCATACG AGCACCTCCA GCCTGAACAG    2270

AAGCTCTTAC TCTTTCCTAT TTCAGTGTTA CCTGTGTGCT TGGTCTGTTT GACTTTACGC    2330

CCATCTCAGG ACACTTCCGT AGACTGTTTA GGTTCCCCTG TCAAATATCA GTTACCCACT    2390

CGGTCCCAGT TTTGTTGCCC CAGAAAGGGA TGTTATTATC CTTGGGGGCT CCCAGGGCAA    2450

GGGTTAAGGC CTGAATCATG AGCCTGCTGG AAGCCCAGCC CCTACTGCTG TGAACCCTGG    2510

GGCCTGACTG CTCAGAACTT GCTGCTGTCT TGTTGCGGAT GGATGGAAGG TTGGATGGAT    2570

GGGTGGATGG CCGTGGATGG CCGTGGATGC GCAGTGCCTT GCATACCCAA ACCAGGTGGG    2630

AGCGTTTTGT TGAGCATGAC ACCTGCAGCA GGAATATATG TGTGCCTATT TGTGTGGACA    2690

AAAATATTTA CACTTAGGGT TTGGAGCTAT TCAAGAAGAA ATGTCACAGA AGCAGCTAAA    2750

CCAAGGACTG AGCACCCTCT GGATTCTGAA TCTCAATATG GGGCAGGGC TGTGCTTGAA     2810

GGCCCTGCTG AGTCATCTGT TAGGGCCTTG GTTCAATAAA GCACTGAGCA AGTTGAGAAA    2870

AAAAAAAAAA AAAAAA                                                   2886
```

(2) INFORMATION FOR SEQ ID NO:3:

(i) SEQUENCE CHARACTERISTICS:
    (A) LENGTH: 2062 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 211..1631

(xi) SEQUENCE DESCRIPTION: SEQ ID NO:3:

```
CAGGAAGACT CTGAGTCCGA CGTTGGCCTA CCCAGTCGGA AGGCAGAGCT GCAATCTAGT      60

TAACTACCTC CTTTCCCCTA GATTTCCTTT CATTCTGCTC AAGTCTTCGC CTGTGTCCGA     120

TCCCTATCTA CTTTCTCTCC TCTTGTAGCA AGCCTCAGAC TCCAGGCTTG AGCTAGGTTT     180

TGTTTTTCTC CTGGTGAGAA TTCGAAGACC ATG TCT ACG GAA CTC TTC TCA TCC     234
                                   Met Ser Thr Glu Leu Phe Ser Ser
                                    1               5

ACA AGA GAG GAA GGA AGC TCT GGC TCA GGA CCC AGT TTT AGG TCT AAT      282
Thr Arg Glu Glu Gly Ser Ser Gly Ser Gly Pro Ser Phe Arg Ser Asn
 10              15                  20

CAA AGG AAA ATG TTA AAC CTG CTC CTG GAG AGA GAC ACT TCC TTT ACC      330
Gln Arg Lys Met Leu Asn Leu Leu Leu Glu Arg Asp Thr Ser Phe Thr
 25              30                  35                  40

GTC TGT CCA GAT GTC CCT AGA ACT CCA GTG GGC AAA TTT CTT GGT GAT      378
Val Cys Pro Asp Val Pro Arg Thr Pro Val Gly Lys Phe Leu Gly Asp
             45                  50                  55

TCT GCA AAC CTA AGC ATT TTG TCT GGA GGA ACC CCA AAA TGT TGC CTC      426
Ser Ala Asn Leu Ser Ile Leu Ser Gly Gly Thr Pro Lys Cys Cys Leu
         60                  65                  70

GAT CTT TCG AAT CTT AGC AGT GGG GAG ATA ACT GCC ACT CAG CTT ACC      474
Asp Leu Ser Asn Leu Ser Ser Gly Glu Ile Thr Ala Thr Gln Leu Thr
```

```
                         75                    80                    85
ACT TCT GCA GAC CTT GAT GAA ACT GGT CAC CTG GAT TCT TCA GGA CTT      522
Thr Ser Ala Asp Leu Asp Glu Thr Gly His Leu Asp Ser Ser Gly Leu
        90                    95                   100

CAG GAA GTG CAT TTA GCT GGG ATG AAT CAT GAC CAG CAC CTA ATG AAA      570
Gln Glu Val His Leu Ala Gly Met Asn His Asp Gln His Leu Met Lys
105                  110                   115                  120

TGT AGC CCA GCA CAG CTT CTT TGT AGC ACT CCG AAT GGT TTG GAC CGT      618
Cys Ser Pro Ala Gln Leu Leu Cys Ser Thr Pro Asn Gly Leu Asp Arg
                125                   130                  135

GGC CAT AGA AAG AGA GAT GCA ATG TGT AGT TCA TCT GCA AAT AAA GAA      666
Gly His Arg Lys Arg Asp Ala Met Cys Ser Ser Ser Ala Asn Lys Glu
                140                   145                  150

AAT GAC AAT GGA AAC TTG GTG GAC AGT GAA ATG AAA TAT TTG GGC AGT      714
Asn Asp Asn Gly Asn Leu Val Asp Ser Glu Met Lys Tyr Leu Gly Ser
            155                   160                  165

CCC ATT ACT ACT GTT CCA AAA TTG GAT AAA AAT CCA AAC CTA GGA GAA      762
Pro Ile Thr Thr Val Pro Lys Leu Asp Lys Asn Pro Asn Leu Gly Glu
    170                   175                  180

GAC CAG GCA GAA GAG ATT TCA GAT GAA TTA ATG GAG TTT TCC CTG AAA      810
Asp Gln Ala Glu Glu Ile Ser Asp Glu Leu Met Glu Phe Ser Leu Lys
185                  190                   195                  200

GAT CAA GAA GCA AAG GTG AGC AGA AGT GGC CTA TAT CGC TCC CCG TCG      858
Asp Gln Glu Ala Lys Val Ser Arg Ser Gly Leu Tyr Arg Ser Pro Ser
                205                   210                  215

ATG CCA GAG AAC TTG AAC AGG CCA AGA CTG AAG CAG GTG GAA AAA TTC      906
Met Pro Glu Asn Leu Asn Arg Pro Arg Leu Lys Gln Val Glu Lys Phe
            220                   225                  230

AAG GAC AAC ACA ATA CCA GAT AAA GTT AAA AAA AAG TAT TTT TCT GGC      954
Lys Asp Asn Thr Ile Pro Asp Lys Val Lys Lys Lys Tyr Phe Ser Gly
            235                   240                  245

CAA GGA AAG CTC AGG AAG GGC TTA TGT TTA AAG AAG ACA GTC TCT CTG     1002
Gln Gly Lys Leu Arg Lys Gly Leu Cys Leu Lys Lys Thr Val Ser Leu
    250                   255                  260

TGT GAC ATT ACT ATC ACT CAG ATG CTG GAG GAA GAT TCT AAC CAG GGG     1050
Cys Asp Ile Thr Ile Thr Gln Met Leu Glu Glu Asp Ser Asn Gln Gly
265                  270                   275                  280

CAC CTG ATT GGT GAT TTT TCC AAG GTA TGT GCG CTG CCA ACC GTG TCA     1098
His Leu Ile Gly Asp Phe Ser Lys Val Cys Ala Leu Pro Thr Val Ser
                285                   290                  295

GGG AAA CAC CAA GAT CTG AAG TAT GTC AAC CCA GAA ACA GTG GCT GCC     1146
Gly Lys His Gln Asp Leu Lys Tyr Val Asn Pro Glu Thr Val Ala Ala
                300                   305                  310

TTA CTG TCG GGG AAG TTC CAG GGT CTG ATT GAG AAG TTT TAT GTC ATT     1194
Leu Leu Ser Gly Lys Phe Gln Gly Leu Ile Glu Lys Phe Tyr Val Ile
            315                   320                  325

GAT TGT CGC TAT CCA TAT GAG TAT CTG GGA GGA CAC ATC CAG GGA GCC     1242
Asp Cys Arg Tyr Pro Tyr Glu Tyr Leu Gly Gly His Ile Gln Gly Ala
        330                   335                  340

TTA AAC TTA TAT AGT CAG GAA GAA CTG TTT AAC TTC TTT CTG AAG AAG     1290
Leu Asn Leu Tyr Ser Gln Glu Glu Leu Phe Asn Phe Phe Leu Lys Lys
345                  350                   355                  360

CCC ATC GTC CCT TTG GAC ACC CAG AAG AGA ATA ATC ATC GTG TTC CAC     1338
Pro Ile Val Pro Leu Asp Thr Gln Lys Arg Ile Ile Ile Val Phe His
                365                   370                  375

TGT GAA TTC TCC TCA GAG AGG GGC CCC CGA ATG TGC CGC TGT CTG CGT     1386
Cys Glu Phe Ser Ser Glu Arg Gly Pro Arg Met Cys Arg Cys Leu Arg
            380                   385                  390

GAA GAG GAC AGG TCT CTG AAC CAG TAT CCT GCA TTG TAC TAC CCA GAG     1434
```

-continued

```
Glu Glu Asp Arg Ser Leu Asn Gln Tyr Pro Ala Leu Tyr Tyr Pro Glu
        395                 400                 405

CTA TAT ATC CTT AAA GGC GGC TAC AGA GAC TTC TTT CCA GAA TAT ATG    1482
Leu Tyr Ile Leu Lys Gly Gly Tyr Arg Asp Phe Phe Pro Glu Tyr Met
    410                 415                 420

GAA CTG TGT GAA CCA CAG AGC TAC TGC CCT ATG CAT CAT CAG GAC CAC    1530
Glu Leu Cys Glu Pro Gln Ser Tyr Cys Pro Met His His Gln Asp His
425                 430                 435                 440

AAG ACT GAG TTG CTG AGG TGT CGA AGC CAG AGC AAA GTG CAG GAA GGG    1578
Lys Thr Glu Leu Leu Arg Cys Arg Ser Gln Ser Lys Val Gln Glu Gly
                445                 450                 455

GAG CGG CAG CTG CGG GAG CAG ATT GCC CTT CTG GTG AAG GAC ATG AGC    1626
Glu Arg Gln Leu Arg Glu Gln Ile Ala Leu Leu Val Lys Asp Met Ser
            460                 465                 470

CCA TG ATAACATTCC AGCCACTGGC TGCTAACAAG TCACCAAAAA GACACTGCAG      1681
Pro

AAACCCTGAG CAGAAAGAGG CCTTCTGGAT GGCCAAACCC AAGATTATTA AAAGATGTCT  1741

CTGCAAACCA ACAGGCTACC AACTTGTATC CAGGCCTGGG AATGGATTAG GTTTCAGCAG  1801

AGCTGAAAGC TGGTGGCCAG AGTCCTGGAG CTGGCTCTAT AAGGCAGCCT TGAGTGCATA  1861

GAGATTTGTA TTGGTTCAGG GAACTCTGGC ATTCCTTTTC CCAACTCCTC ATGTCTTCTC  1921

ACAAGCCAGC CAACTCTTTC TCTCTGGGCT TCGGGCTATG CAAGAGCGTT GTCTACCTTC  1981

TTTCTTTGTA TTTTCCTTCT TTGTTTCCCC CTCTTTCTTT TTTAAAAATG GAAAAATAAA  2041

CACTACAGAA TGAGAAAAAA A                                           2062

(2) INFORMATION FOR SEQ ID NO:4:

(i) SEQUENCE CHARACTERISTICS:
        (A) LENGTH: 2977 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 130..2073

(xi) SEQUENCE DESCRIPTION: SEQ ID NO:4:

CCGAATGTGA CCGCCTCCCG CTCCCTCACC CGCCGCGGGG AGGAGGAGCG GGCGAGAAGC    60

TGCCGCCGAA CGACAGGACG TTGGGGCGGC CTGGCTCCCT CAGGTTTAAG AATTGTTTAA   120

GCTGCATCA ATG GAG CAC ATA CAG GGA GCT TGG AAG ACG ATC AGC AAT      168
          Met Glu His Ile Gln Gly Ala Trp Lys Thr Ile Ser Asn
          1               5                   10

GGT TTT GGA TTC AAA GAT GCC GTG TTT GAT GGC TCC AGC TGC ATC TCT    216
Gly Phe Gly Phe Lys Asp Ala Val Phe Asp Gly Ser Ser Cys Ile Ser
    15                  20                  25

CCT ACA ATA GTT CAG CAG TTT GGC TAT CAG CGC CGG GCA TCA GAT GAT    264
Pro Thr Ile Val Gln Gln Phe Gly Tyr Gln Arg Arg Ala Ser Asp Asp
30                  35                  40                  45

GGC AAA CTC ACA GAT CCT TCT AAG ACA AGC AAC ACT ATC CGT GTT TTC    312
Gly Lys Leu Thr Asp Pro Ser Lys Thr Ser Asn Thr Ile Arg Val Phe
                50                  55                  60

TTG CCG AAC AAG CAA AGA ACA GTG GTC AAT GTG CGA AAT GGA ATG AGC    360
Leu Pro Asn Lys Gln Arg Thr Val Val Asn Val Arg Asn Gly Met Ser
            65                  70                  75

TTG CAT GAC TGC CTT ATG AAA GCA CTC AAG GTG AGG GGC CTG CAA CCA    408
Leu His Asp Cys Leu Met Lys Ala Leu Lys Val Arg Gly Leu Gln Pro
```

```
              80                    85                    90
GAG TGC TGT GCA GTG TTC AGA CTT CTC CAC GAA CAC AAA GGT AAA AAA          456
Glu Cys Cys Ala Val Phe Arg Leu Leu His Glu His Lys Gly Lys Lys
         95                   100                   105

GCA CGC TTA GAT TGG AAT ACT GAT GCT GCG TCT TTG ATT GGA GAA GAA          504
Ala Arg Leu Asp Trp Asn Thr Asp Ala Ala Ser Leu Ile Gly Glu Glu
110                   115                   120                   125

CTT CAA GTA GAT TTC CTG GAT CAT GTT CCC CTC ACA ACA CAC AAC TTT          552
Leu Gln Val Asp Phe Leu Asp His Val Pro Leu Thr Thr His Asn Phe
                 130                   135                   140

GCT CGG AAG ACG TTC CTG AAG CTT GCC TTC TGT GAC ATC TGT CAG AAA          600
Ala Arg Lys Thr Phe Leu Lys Leu Ala Phe Cys Asp Ile Cys Gln Lys
             145                   150                   155

TTC CTG CTC AAT GGA TTT CGA TGT CAG ACT TGT GGC TAC AAA TTT CAT          648
Phe Leu Leu Asn Gly Phe Arg Cys Gln Thr Cys Gly Tyr Lys Phe His
         160                   165                   170

GAG CAC TGT AGC ACC AAA GTA CCT ACT ATG TGT GTG GAC TGG AGT AAC          696
Glu His Cys Ser Thr Lys Val Pro Thr Met Cys Val Asp Trp Ser Asn
     175                   180                   185

ATC AGA CAA CTC TTA TTG TTT CCA AAT TCC ACT ATT GGT GAT AGT GGA          744
Ile Arg Gln Leu Leu Leu Phe Pro Asn Ser Thr Ile Gly Asp Ser Gly
190                   195                   200                   205

GTC CCA GCA CTA CCT TCT TTG ACT ATG CGT CGT ATG CGA GAG TCT GTT          792
Val Pro Ala Leu Pro Ser Leu Thr Met Arg Arg Met Arg Glu Ser Val
                 210                   215                   220

TCC AGG ATG CCT GTT AGT TCT CAG CAC AGA TAT TCT ACA CCT CAC GCC          840
Ser Arg Met Pro Val Ser Ser Gln His Arg Tyr Ser Thr Pro His Ala
             225                   230                   235

TTC ACC TTT AAC ACC TCC AGT CCC TCA TCT GAA GGT TCC CTC TCC CAG          888
Phe Thr Phe Asn Thr Ser Ser Pro Ser Ser Glu Gly Ser Leu Ser Gln
         240                   245                   250

AGG CAG AGG TCG ACA TCC ACA CCT AAT GTC CAC ATG GTC AGC ACC ACG          936
Arg Gln Arg Ser Thr Ser Thr Pro Asn Val His Met Val Ser Thr Thr
     255                   260                   265

CTG CCT GTG GAC AGC AGG ATG ATT GAG GAT GCA ATT CGA AGT CAC AGC          984
Leu Pro Val Asp Ser Arg Met Ile Glu Asp Ala Ile Arg Ser His Ser
270                   275                   280                   285

GAA TCA GCC TCA CCT TCA GCC CTG TCC AGT AGC CCC AAC AAT CTG AGC         1032
Glu Ser Ala Ser Pro Ser Ala Leu Ser Ser Ser Pro Asn Asn Leu Ser
                 290                   295                   300

CCA ACA GGC TGG TCA CAG CCG AAA ACC CCC GTG CCA GCA CAA AGA GAG         1080
Pro Thr Gly Trp Ser Gln Pro Lys Thr Pro Val Pro Ala Gln Arg Glu
             305                   310                   315

CGG GCA CCA GTA TCT GGG ACC CAG GAG AAA AAC AAA ATT AGG CCT CGT         1128
Arg Ala Pro Val Ser Gly Thr Gln Glu Lys Asn Lys Ile Arg Pro Arg
         320                   325                   330

GGA CAG AGA GAT TCA AGC TAT TAT TGG GAA ATA GAA GCC AGT GAA GTG         1176
Gly Gln Arg Asp Ser Ser Tyr Tyr Trp Glu Ile Glu Ala Ser Glu Val
     335                   340                   345

ATG CTG TCC ACT CGG ATT GGG TCA GGC TCT TTT GGA ACT GTT TAT AAG         1224
Met Leu Ser Thr Arg Ile Gly Ser Gly Ser Phe Gly Thr Val Tyr Lys
350                   355                   360                   365

GGT AAA TGG CAC GGA GAT GTT GCA GTA AAG ATC CTA AAG GTT GTC GAC         1272
Gly Lys Trp His Gly Asp Val Ala Val Lys Ile Leu Lys Val Val Asp
                 370                   375                   380

CCA ACC CCA GAG CAA TTC CAG GCC TTC AGG AAT GAG GTG GCT GTT CTG         1320
Pro Thr Pro Glu Gln Phe Gln Ala Phe Arg Asn Glu Val Ala Val Leu
             385                   390                   395

CGC AAA ACA CGG CAT GTG AAC ATT CTG CTT TTC ATG GGG TAC ATG ACA         1368
```

-continued

```
                    Arg Lys Thr Arg His Val Asn Ile Leu Leu Phe Met Gly Tyr Met Thr
                                    400                 405                 410

AAG GAC AAC CTG GCA ATT GTG ACC CAG TGG TGC GAG GGC AGC AGC CTC              1416
Lys Asp Asn Leu Ala Ile Val Thr Gln Trp Cys Glu Gly Ser Ser Leu
            415                 420                 425

TAC AAA CAC CTG CAT GTC CAG GAG ACC AAG TTT CAG ATG TTC CAG CTA              1464
Tyr Lys His Leu His Val Gln Glu Thr Lys Phe Gln Met Phe Gln Leu
430                 435                 440                 445

ATT GAC ATT GCC CGG CAG ACG GCT CAG GGA ATG GAC TAT TTG CAT GCA              1512
Ile Asp Ile Ala Arg Gln Thr Ala Gln Gly Met Asp Tyr Leu His Ala
                450                 455                 460

AAG AAC ATC ATC CAT AGA GAC ATG AAA TCC AAC AAT ATA TTT CTC CAT              1560
Lys Asn Ile Ile His Arg Asp Met Lys Ser Asn Asn Ile Phe Leu His
            465                 470                 475

GAA GGC TTA ACA GTG AAA ATT GGA GAT TTT GGT TTG GCA ACA GTA AAG              1608
Glu Gly Leu Thr Val Lys Ile Gly Asp Phe Gly Leu Ala Thr Val Lys
        480                 485                 490

TCA CGC TGG AGT GGT TCT CAG CAG GTT GAA CAA CCT ACT GGC TCT GTC              1656
Ser Arg Trp Ser Gly Ser Gln Gln Val Glu Gln Pro Thr Gly Ser Val
    495                 500                 505

CTC TGG ATG GCC CCA GAG GTG ATC CGA ATG CAG GAT AAC AAC CCA TTC              1704
Leu Trp Met Ala Pro Glu Val Ile Arg Met Gln Asp Asn Asn Pro Phe
510                 515                 520                 525

AGT TTC CAG TCG GAT GTC TAC TCC TAT GGC ATC GTA TTG TAT GAA CTG              1752
Ser Phe Gln Ser Asp Val Tyr Ser Tyr Gly Ile Val Leu Tyr Glu Leu
                530                 535                 540

ATG ACG GGG GAG CTT CCT TAT TCT CAC ATC AAC AAC CGA GAT CAG ATC              1800
Met Thr Gly Glu Leu Pro Tyr Ser His Ile Asn Asn Arg Asp Gln Ile
            545                 550                 555

ATC TTC ATG GTG GGC CGA GGA TAT GCC TCC CCA GAT CTT AGT AAG CTA              1848
Ile Phe Met Val Gly Arg Gly Tyr Ala Ser Pro Asp Leu Ser Lys Leu
        560                 565                 570

TAT AAG AAC TGC CCC AAA GCA ATG AAG AGG CTG GTA GCT GAC TGT GTG              1896
Tyr Lys Asn Cys Pro Lys Ala Met Lys Arg Leu Val Ala Asp Cys Val
    575                 580                 585

AAG AAA GTA AAG GAA GAG AGG CCT CTT TTT CCC CAG ATC CTG TCT TCC              1944
Lys Lys Val Lys Glu Glu Arg Pro Leu Phe Pro Gln Ile Leu Ser Ser
590                 595                 600                 605

ATT GAG CTG CTC CAA CAC TCT CTA CCG AAG ATC AAC CGG AGC GCT TCC              1992
Ile Glu Leu Leu Gln His Ser Leu Pro Lys Ile Asn Arg Ser Ala Ser
                610                 615                 620

GAG CCA TCC TTG CAT CGG GCA GCC CAC ACT GAG GAT ATC AAT GCT TGC              2040
Glu Pro Ser Leu His Arg Ala Ala His Thr Glu Asp Ile Asn Ala Cys
            625                 630                 635

ACG CTG ACC ACG TCC CCG AGG CTG CCT GTC TTC TAGTTGACTT TGCACCTGTC            2093
Thr Leu Thr Thr Ser Pro Arg Leu Pro Val Phe
        640                 645

TTCAGGCTGC CAGGGGAGGA GGAGAAGCCA GCAGGCACCA CTTTTCTGCT CCCTTTCTCC            2153

AGAGGCAGAA CACATGTTTT CAGAGAAGCT CTGCTAAGGA CCTTCTAGAC TGCTCACAGG            2213

GCCTTAACTT CATGTTGCCT TCTTTTCTAT CCCTTTGGGC CCTGGGAGAA GGAAGCCATT            2273

TGCAGTGCTG GTGTGTCCTG CTCCCTCCCC ACATTCCCCA TGCTCAAGGC CCAGCCTTCT            2333

GTAGATGCGC AAGTGGATGT TGATGGTAGT ACAAAAAGCA GGGGCCCAGC CCAGCTGTT             2393

GGCTACATGA GTATTTAGAG GAAGTAAGGT AGCAGGCAGT CCAGCCCTGA TGTGGAGACA            2453

CATGGGATTT TGGAAATCAG CTTCTGGAGG AATGCATGTC ACAGGCGGGA CTTTCTTCAG            2513

AGAGTGGTGC AGCGCCAGAC ATTTTGCACA TAAGGCACCA AACAGCCCAG GACTGCCGAG            2573
```

-continued

```
ACTCTGGCCG CCCGAAGGAG CCTGCTTTGG TACTATGGAA CTTTTCTTAG GGGACACGTC     2633

CTCCTTTCAC AGCTTCTAAG GTGTCCAGTG CATTGGGATG GTTTTCCAGG CAAGGCACTC     2693

GGCCAATCCG CATCTCAGCC CTCTCAGGAG CAGTCTTCCA TCATGCTGAA TTTTGTCTTC     2753

CAGGAGCTGC CCCTATGGGG CGGGCCGCAG GGCCAGCCTG TTTCTCTAAC AAACAAACAA     2813

ACAAACAGCC TTGTTTCTCT AGTCACATCA TGTGTATACA AGGAAGCCAG GAATACAGGT     2873

TTTCTTGATG ATTTGGGTTT TAATTTTGTT TTTATTGCAC CTGACAAAAT ACAGTTATCT     2933

GATGGTCCCT CAATTATGTT ATTTTAATAA AATAAATTAA ATTT                     2977
```

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Cys Met Tyr Ser Arg Leu Lys Lys Leu
1               5

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Cys Ser Arg Leu Gln Asp Gln
1               5